US008945727B2

(12) United States Patent
Kwong et al.

(10) Patent No.: US 8,945,727 B2
(45) Date of Patent: *Feb. 3, 2015

(54) ORGANOSELENIUM MATERIALS AND THEIR USES IN ORGANIC LIGHT EMITTING DEVICES

(71) Applicant: Universal Display Corporation, Ewing, NJ (US)

(72) Inventors: Raymond Kwong, Plainsboro, NJ (US); Bin Ma, Plainsboro, NJ (US); Chuanjun Xia, Lawrenceville, NJ (US); Chun Lin, Langhorne, PA (US)

(73) Assignee: Universal Display Corporation, Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/775,584

(22) Filed: Feb. 25, 2013

(65) Prior Publication Data

US 2013/0168660 A1    Jul. 4, 2013

Related U.S. Application Data

(63) Continuation of application No. 12/565,966, filed on Sep. 24, 2009, now Pat. No. 8,426,035.

(60) Provisional application No. 61/100,229, filed on Sep. 25, 2008.

(51) Int. Cl.
| | |
|---|---|
| *H01L 51/54* | (2006.01) |
| *C09K 11/06* | (2006.01) |
| *C07D 345/00* | (2006.01) |
| *C07D 209/82* | (2006.01) |
| *C07D 401/14* | (2006.01) |
| *H01L 51/00* | (2006.01) |
| *C07D 421/14* | (2006.01) |
| *H01L 51/50* | (2006.01) |

(52) U.S. Cl.
CPC .......... *H01L 51/0072* (2013.01); *C07D 345/00* (2013.01); *C07D 421/14* (2013.01); *H01L 51/0061* (2013.01); *H01L 51/0071* (2013.01); *H01L 51/0067* (2013.01); *H01L 51/5012* (2013.01); *Y10S 428/917* (2013.01)
USPC ........... 428/690; 428/917; 313/502; 313/504; 540/1

(58) Field of Classification Search
None
See application file for complete search history.

(56) References Cited

U.S. PATENT DOCUMENTS

| | | |
|---|---|---|
| 4,769,292 A | 9/1988 | Tang et al. |
| 5,121,029 A | 6/1992 | Hosokawa et al. |
| 5,130,603 A | 7/1992 | Tokailin et al. |
| 5,247,190 A | 9/1993 | Friend |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,310,360 B1 | 10/2001 | Forrest et al. |
| 6,337,102 B1 | 1/2002 | Forrest et al. |
| 6,468,819 B1 | 10/2002 | Kim et al. |
| 6,548,956 B2 | 4/2003 | Forrest et al. |
| 6,576,134 B1 | 6/2003 | Agner |
| 6,602,540 B2 | 8/2003 | Gu et al. |
| 6,830,828 B2 | 12/2004 | Thompson et al. |
| 6,835,469 B2 | 12/2004 | Kwong et al. |
| 6,863,997 B2 | 3/2005 | Thompson et al. |
| 6,869,695 B2 | 3/2005 | Thompson et al. |
| 7,279,704 B2 | 10/2007 | Walters et al. |
| 7,431,968 B1 | 10/2008 | Shtein et al. |
| 2002/0034656 A1 | 3/2002 | Thompson et al. |
| 2002/0115079 A1 | 8/2002 | Okamoto et al. |
| 2002/0182441 A1 | 12/2002 | Lamansky et al. |
| 2003/0072964 A1 | 4/2003 | Kwong et al. |
| 2003/0230980 A1 | 12/2003 | Forrest et al. |
| 2004/0174116 A1 | 9/2004 | Lu et al. |
| 2005/0079387 A1* | 4/2005 | Lee et al. ...................... 428/690 |
| 2006/0222886 A1 | 10/2006 | Kwong et al. |
| 2006/0280965 A1 | 12/2006 | Kwong |
| 2007/0278938 A1* | 12/2007 | Yabunouchi et al. ......... 313/504 |
| 2008/0100207 A1 | 5/2008 | Park et al. |

FOREIGN PATENT DOCUMENTS

| | | | |
|---|---|---|---|
| EP | 0 273 643 | 7/1988 | |
| EP | 1 894 923 | 3/2008 | |
| EP | 1962354 A1 * | 8/2008 | |
| JP | 63211265 | 9/1988 | |
| JP | 06212151 A * | 8/1994 | ............. C09K 11/06 |
| JP | 07053950 A * | 2/1995 | ............. C09K 11/06 |

(Continued)

OTHER PUBLICATIONS

Machine translation of JP06-212151. Date of publication: Aug. 2, 1994.*
Machine translation of JP07-053950. Date of publication: Feb. 28, 1995.*
Mohanakrishnan et al. "Synthesis of 1,3-diarylbenzo[c]selenophenes" Tetrahedron Letters 2005, 46, 7201-7204. Date of online publication: Sep. 2, 2005.*
Huang et al. "Organic electroluminescent derivatives containing dibenzothiophene and diarylamine segments" J. Mater. Chem. 2005, 15, 3233-3240. Date of online publication: Jun. 30, 3005.*
Osuna et al. "Thiophene- and Selenophene-Based Heteroacenes: Combined Quantum Chemical DFT and Spectroscropic Raman and UV-Vis-NIR Study" J. Phys. Chem. B 2007, 111, 7488-7496. Date of online publication: Jun. 12, 2007.*

(Continued)

*Primary Examiner* — Andrew K Bohaty
(74) *Attorney, Agent, or Firm* — Duane Morris LLP

(57) ABSTRACT

The present invention provides organoselenium compounds comprising dibenzoselenophene, benzo[b]selenophene or benzo[c]selenophene and their uses in organic light emitting devices.

2 Claims, 2 Drawing Sheets

(56) References Cited

FOREIGN PATENT DOCUMENTS

| JP | 2000 252065 | 9/2000 |
|---|---|---|
| WO | WO 02/074015 | 9/2002 |
| WO | WO 2007069569 A1 * | 6/2007 |

OTHER PUBLICATIONS

Adachi et al., "Nearly 100% Internal Phosphorescent Efficiency in an Organic Light Emitting Device" J. Appl. Phys. 90:5048, 2001.
Adachi et al., 1989, "Organic electroluminescent device having a hole conductor as an emitting layer", Appl. Phys. Lett.: 55(15):1489-1491.
Adachi et al., 2001, "High-efficiency red electrophosphorescence devices" Appl. Phys. Lett. 78 : 1622-1624.
Aonuma et al., 2007, "Material design of hole transport materials capable of thick-film formation in organic light emitting diodes", Appl. Phys. Lett. 90:183503-183505.
Baldo et al., "High-efficiency fluorescent organic light-emitting devices using a phosphorescent sensitizer", Nature. 403(6771):750-3, 2000.
Baldo et al., "Highly Efficient Phosphorescent Emission from Organic Electroluminescent Devices", Nature 395:151-154, 1998.
Baldo et al., "Very high efficiency green organic light-emitting devices based on electrophosphorescence," Appl. Phys.Lett. 75(3):4-6, 1999.
Chang et al.,, 2008, "Highly Efficient Blue-Emitting Iridium(III) Carbene Complexes and Phosphorescent OLEDS", Angew. Chem. Int. Ed. 47:4542-4545.
Chen et al., "Recent Developments in Molecular Organic Electroluminescent Materials", Macromol. Symp. 125: 1-48, 1997.
Dakova et al., 1992, "Electrochemical Behavior of Seleno-Organic Compounds—Part 3. Electrochemical Study of Dibenzo(c,e)-1,2-Diselenine in Acetonitrile Medium", Electrochimica Acta 37(11):2077-2082.
Dakova et al., 1992, "Electrochemical Behavior of Seleno-Organic Compounds—Part 2. Benzo(b)Selenophene and Dibenzo(b,d)Selenophene", Electrochimica Acta 37(8):1453-1456.
Gao et al. , 1999, "Bright-blue electroluminescence from a silyl-substituted ter-(phenylene-vinylene) derivative", Appl. Phys. Lett. 74, 865.
Guo et al., 2000, "Highly efficient electrophosphorescent polymer light-emitting devices", Org. Electron 1:15-20.
Hamada et al., 1993, "High Luminance in Organic Electroluminescent Devices with Bis(10-hydroxybenzo[h]quinolinato)beryllium as an Emitter", Chem. Lett. 905-906.
Holmes et al. , 2003, Blue organic electrophosphorescence using exothermic host—guest energy transfer, Appl. Phys. Lett. 82, 2422-2424.
Huang et al., 2004, "Highly Phosphorescent Bis-Cyclometalated Iridium Complexes Containing Benzoimidazole-Based Ligands", Chem Mater. 16: 2480-2488.
Huang et al., 2007, "Highly Efficient Red-Emission Polymer Phosphorescent Light-Emitting Diodes Based on Two Novel Tris(1-phenylisoqui9nolinato-C2,N)iridium(III) Derivatives", Adv. Mater. 19: 739-743.
Huang et al., 2007, "Highly Efficient Red-Emission Polymer Phosphorescent Light-Emitting Diodes Based on Two Novel Tris(1-phenylisoquinolinato-C2,N)iridium(III) Derivatives", Adv. Mater. 19:739-743.
Hung and Chen, "Recent progress of molecular organic eletroluminescent materials and devices", Mat. Sci and Eng. R, 39:143-222. , 2002.
Hung et al., 2001, "Anode modification in organic light-emitting diodes by low-frequency plasma polymerization of $CHF_3$", Appl. Phys. Lett. 78:673-675.
Ikai et al., 2001, "Highly efficient phosphorescence from organic light-emitting devices with an exciton-block layer", Appl. Phys. Lett. 79, 156.

Ikeda et al., 2006, "P-185: Low-Drive-Voltage OLEDs with a Buffer Layer Having Molybdenum Oxide", SID Symposium Digest, vol. XXXVII, Book 1, pp. 923-926.
Inada et al., 1993, 1,3,5-Tris[4-(diphenylamino)phenyl] benzene and its Methyl-substituted Derivatives as a Novel Class of Amorphous Molecular Materials, J. Mater. Chem 3,319-320.
Kanno et al. , 2007, "Highly efficient and stable red phosphorescent organic light-emitting device using bis[2-(2-benzothiazoyl)phenolato]zinc(II) as host material", Appl. Phys. Lett 90, 123509.
Kido et al., 1993, "1,2,4-Triazole Derivative as an Electron Transport Layer in Organic Electroluminescent Devices", Jpn. J. Apply.y. Phys. (32) L917-L920.
Kuwabara et al., 1994, "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenylamino)triphenylamine (m-MTDATA), as Hole Transport Materials", Adv. Mater. 6: 677-679.
Kwong et al. , 2002, "High operational stability of electrophosphorescent devices",Appl. Phys. Lett. 81, 162.
Lamansky et al., 2001, "Synthesis and Characterization of P hosphorescent Cyclometalated Iridium Complexes", Inorg. Chem 40:1704-1711.
Lee et al. , 2000, Polymer phosphorescent light-emitting devices doped with tris(2-phenylpyridine) iridium as a triplet emitter, Appl. Phys. Lett. 77:2280-2282.
Lo et al., 2006, "Blue Phosphorescence from Iridium(III) Complexes at Room Temperature", Chem Mater. 18:5119-5129.
Ma et al. , 1999, "Triplet luminescent dinuclear-gold(I) complex-based light-emitting diodes with low turn-on voltage", Appl. Phys. Lett. 74:1361.
McCullough et al., 1950, "A New Synthesis of Dibenzodelenophene", J. Am. Chem. Soc., 72:5753-5754.
Mi et al., 2003, "Thermally Stable Hole-Transporting Material for Organic Light-Emitting Diode: an Isoindole Derivative", Chem. Mater. 15:3148-3151.
Murphy et al., 2000, "Product Class 7:Dibenzoselenophenes", Science of Synthesis, 10(2)265-299.
Murphy et al., 2000, "Product Class 9:Dibenzoselenophenes", Science of Synthesis, 10(2)307-323.
Naka et al., 2000, "Carrier transport properties of organic materials for EL device operation", Synth. Met. 111:331-333.
Nishida et al., 2005, "Preparation, Characterization, and Electroluminescence Characteristics of -α-Diimine-type Platinum(II) Complexes with Perfluorinated Phenyl Groups as Ligands", Chem. Lett. 34:592-593.
Niu et al., 2005, "Highly Efficient Electrophosphorescent Devices with Saturated Red Emission From a Neutral Osmium Complex", Chem Mater. 17:35323536.
Noda et al., 1998, "5,5'-Bis(dimesitylboryl)-2,2'-bithiophene and 5,5"-Bis(dimesitylboryl)-2,2':5',2"-terthiophene as a Novel Family of Electron-Transporting Amorphouse Molecular Materials", J. Am.. Chem. Soc. 120:9714-9715.
Okumoto et al., 2006, "Green fluorescent organic light-emitting device with external quantum efficiency of nearly 10%", Appl. Phys. Lett 89, 063504.
Ostergard et al., 1997, "Langmuir-Blodgett light-emitting diodes of poly(3-hexylthiophene):electro-optical characeristics related to structure", Synth. Met 87:171-177.
Palilis et al., 2003, "High efficiency molecular organic light-emitting diodes based on silole derivatives and their exciplexes", Organic Electronics 4:113-121.
Paulose et al. , 2004, "First Examples of Alkenyl Pyridines as Organic Ligands for Phosphorescent Iridium Complexes", Adv. Mater. 16: 2003-2007.
Ranjan et al., 2003, "Realizing Green Phosphorescent Light-Emitting Materials from Rhenium(I) Pyrazolato Diimine Complexes", Inorg. Chem 42: 1248-1255.
Sakamoto et al., 2000, "Synthesis, Characterization, and Electron-Transport Property of Perfluorinated Phenylene Dendrimers", J. Am. Chem Soc. 122:1832-1833.
Salbeck et al., 1997, "Low molecular organic glasses for blue electroluminescence", Synth. Met. 91:209-215.

(56) References Cited

OTHER PUBLICATIONS

Schatz, 2002, "Product Class 11: Selenophenes", Science of Synthesis 9:423-432.
Shirota et al., 1997, "Starburst molecules based on π-electron systems as materials for organic electroluminescent devices", J. Lumin, 72-74, pp. 985-991.
Sotoyama et al., 2005, "Efficient organic light-emitting diodes with phosphorescent platinum complexes containing $N^{\wedge}C^{\wedge}N$-coordinating tridentate ligand" Appl. Phys. Lett. 86, 153505-153507.
Sun et al., 2007, "High-efficiency white organic light emitting devices with three separate phosphorescent emission layers", Appl. Phys. Lett 91, 263503.
Takizawa et al., 2007, "Phosphorescent Iridium Complexes Based on 2-Phenylimidazo[1,2-a]pyridine Ligands: Tuning of Emission Color toward the Blue Region and Application to Polymer Light-Emitting Devices", Inorg. Chem 46:4308-4319.
Tang et al., 1987, "Organic electroluminescent diodes", Appl. Phys. Lett. 51, 913-915.
Tung et al., 2004, "Highly Efficient Red Phosphorescent Osmium(II) Complexes for OLED Applications", Organometallics 23, 3745-3748. 2004.
Tung et al., 2005, "Organic Light-Emitting Diodes based on Charge-Neutral $Ru^{II}$ Phosphorescent Emittes", Adv. Mater. 17:1059-1064.
Van Slyke et al.,1996,"Organic electroluminescent devices with improved stability", Appl. Phys. Lett. 69:2160-2162.
Wang et al. , 2001, Highly efficient electroluminescent materials based on fluorinated organometallic iridium compounds, Appl. Phys. Lett. 79, 449.
Wong et al., 2005, "A novel class of phosphorescent gold(III) alkynyl-based organic light-emitting devices with tunable colour", Chem. Commun. 2906-2908.
Wong et al., 2006, "Multifunctional Iridium Complexes Based on Carbazole Modules as Highly Efficient electrophosphors", Angew. Chem. Int. Ed. 45: 7800-7803.
International Preliminary Report on Patentability for PCT/US09/058162 mailed on Apr. 7, 2011.
Gaidis et al., 1970, "Biphenylene Insertion Products, Dibenzoselenophene and Diphenyldibenzostannole", J. Org. Chem. 35(8):2811-2813.
Sato et al.,1995, "First Detection of 2,2'-biphenylylenediphenylsulfurane and -Selenurane [10-M-4(C4), M=S, Se] by Low Temperature NMR Experiments and Isolation of the Tellurane" Tetrahedron Letters, 36(16):2803-2806.
Suzuki et al., 1995, "A Convenient Synthesis of Functionalized Dibenzotellurophenes and Related Compounds via the Intramolecular Telluro Coupling Reaction. The positive Effect of Heavy Chalcogen Atoms on the Molecular Hyperpolarizability of a Captodative Conjugation System". J. Org. Chem., 60:5274-5278.
Kimura et al., 1994, "Effect of the Through Space Interaction on the Photolytic Desulfurization or Deselenization and Intramolecular Cyclization Reaction of 1,9-Disubstituted Dibenzochalcogenophenes", J. Org. Chem. 59: 7117-7124.
PCT International Search Report and Written Opinion from PCT/US09/058162 mailed on Mar. 10, 2010.

\* cited by examiner

ORGANOSELENIUM MATERIALS AND THEIR USES IN ORGANIC LIGHT EMITTING DEVICES

RELATED APPLICATION

This application is a continuation application under 35 U.S.C. §120 of prior application Ser. No. 12/565,966 filed Sep. 24, 2009, which claims the benefit under 35 U.S.C. §119(e) of U.S. Provisional Application No. 61/100,229, filed Sep. 25, 2008; each of which is incorporated by reference in its entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organoselenium materials comprising dibenzoselenophene, benzo[b]selenophene or benzo[c]selenophene and their uses in organic light emitting devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure of Formula I:

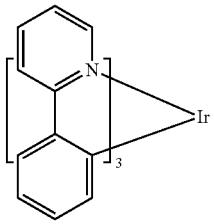

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

The present invention provides an organic light emitting device, comprising an organic layer positioned between an anode layer and a cathode layer. The organic layer comprises an organoselenium material selected from the group consisting of a compound comprising a dibenzoselenophene, a compound comprising a benzo[b]selenophene, and a compound comprising benzo[c]selenophene. Organoselenium compounds that can be used in the organic light emitting device of the invention are disclosed herein below. The invention also provides such organoselenium compounds.

In one embodiment, the organoselenium material is a host material, and the organic layer further comprises a dopant material. The dopant material can be a phosphorescent or fluorescent dopant material. In a preferred embodiment, the dopant material is a phosphorescent dopant material, such as any of the phosphorescent dopant material disclosed in Table 1 below.

In one embodiment, the organic light emitting device of the invention further comprises one or more organic layers selected from the group consisting of a hole injecting layer, an electron injecting layer, a hole transporting layer, an electron transporting layer, a hole blocking layer, an exciton blocking layer, and an electron blocking layer.

In one embodiment, the hole transporting layer or the electron transporting layer comprises an organoselenium material.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols, 5-6, which are incorporated by reference.

Figure 1:
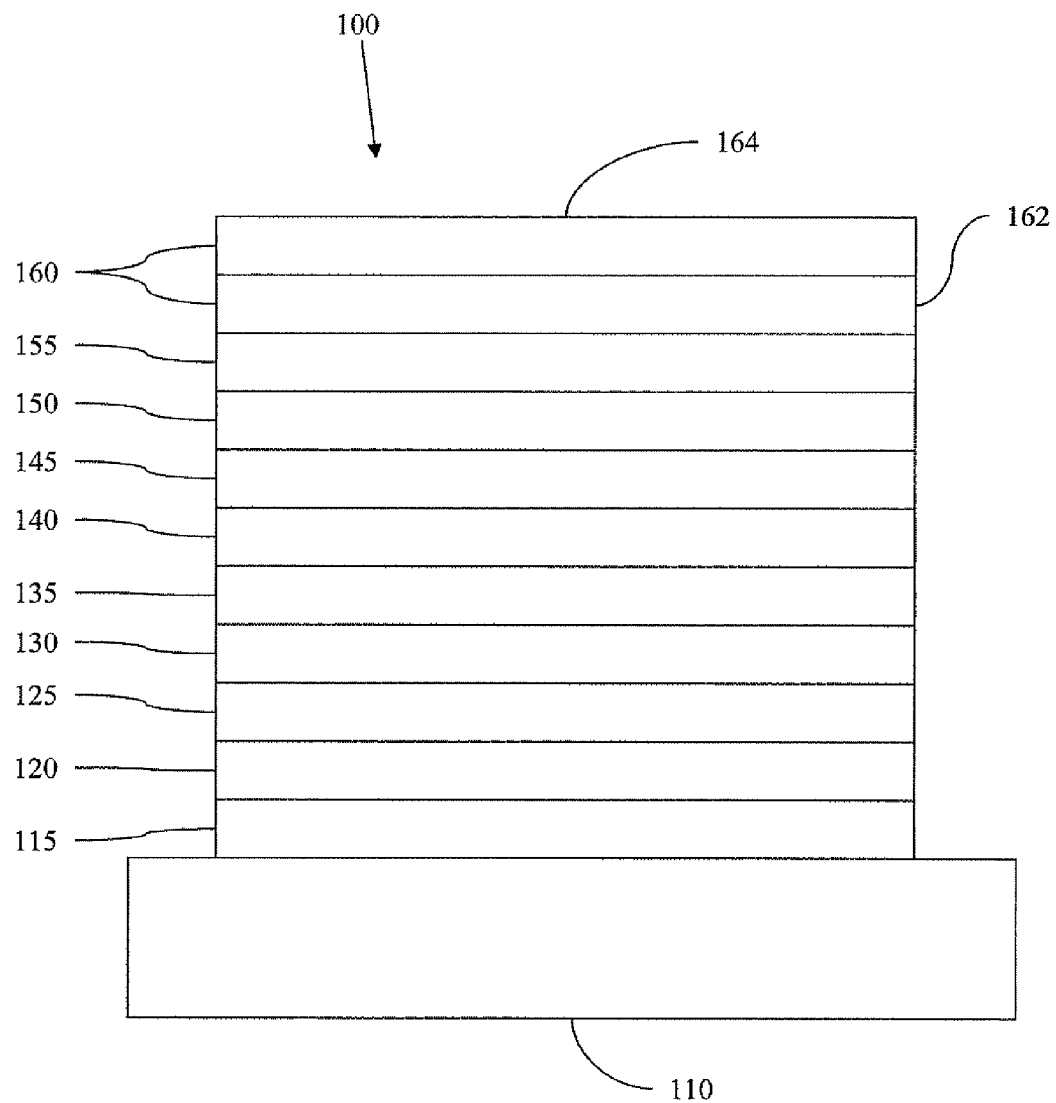
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
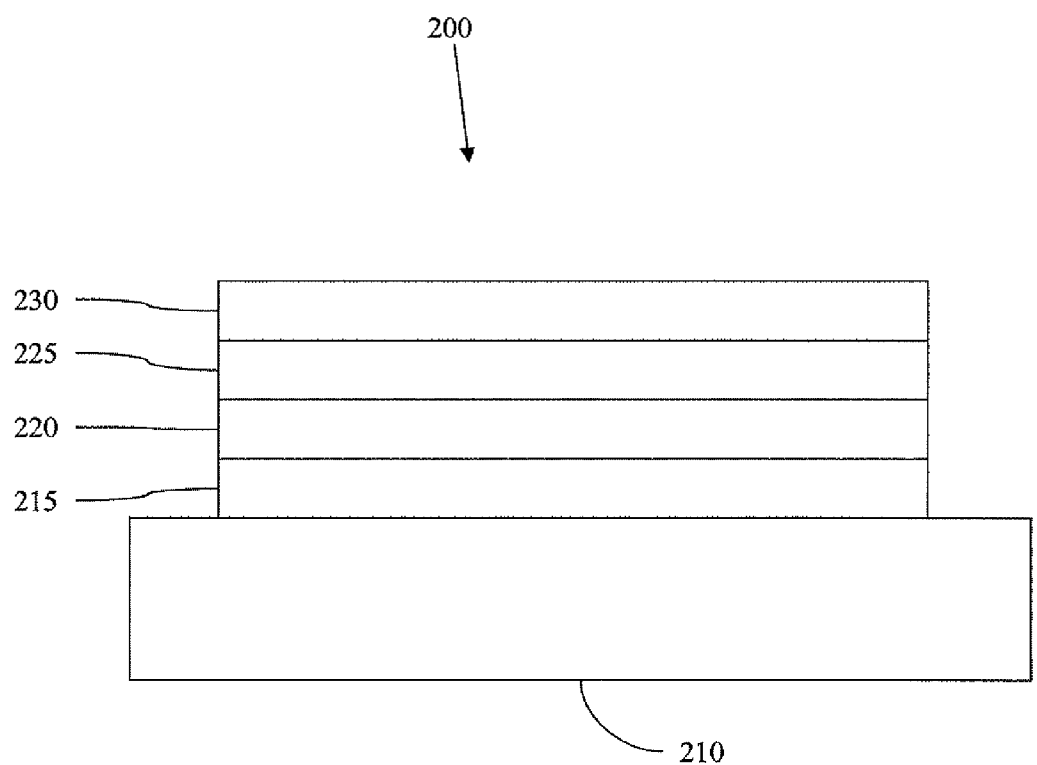
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

The present invention provides an organoselenium compound comprising dibenzoselenophene, benzo[c]selenophene and/or benzo[c]selenophene. The present invention also provides OLED devices in which such material is used, e.g., as a host material.

The organoselenium compound of the invention can comprise one, two, three, four or more dibenzoselenophene moieties, benzo[b]selenophene moieties, benzo[c]selenophene moieties or a mixture thereof. The dibenzoselenophene moieties, benzo[c]selenophene moieties, benzo[c]selenophene moieties or a mixture thereof can be linked directly or through one or more other molecular moieties.

In one embodiment, the organoselenium compound is selected from the groups consisting of

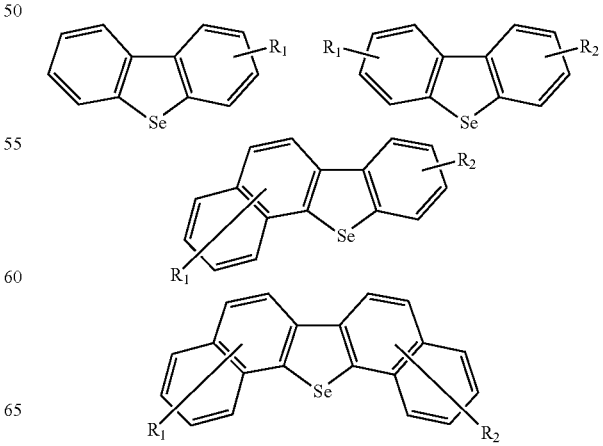

7
-continued
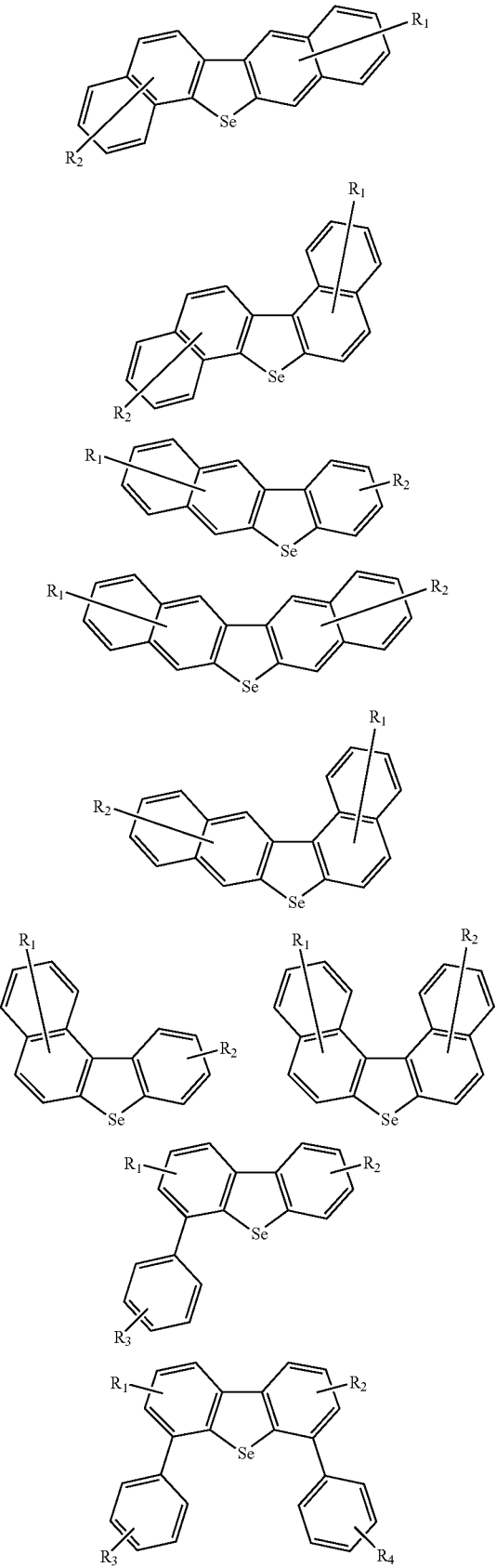
8
-continued
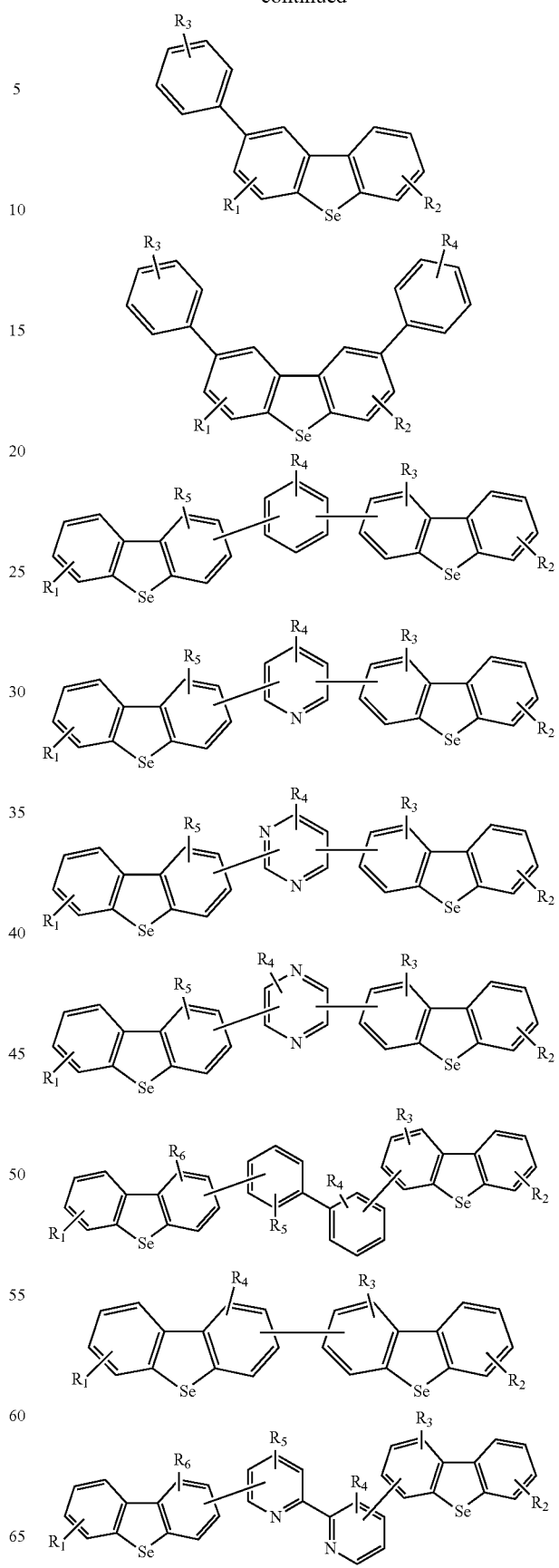

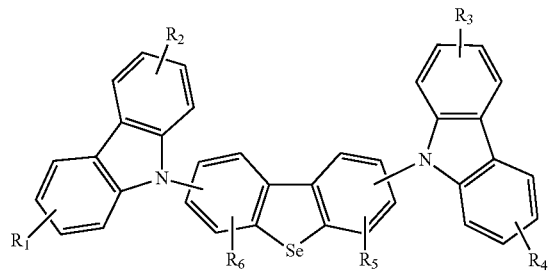
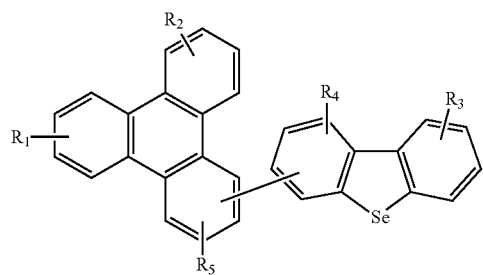
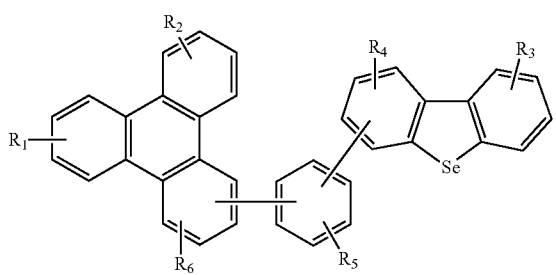
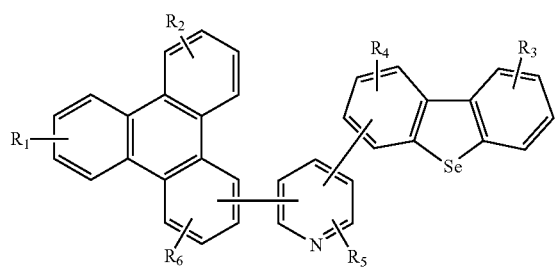
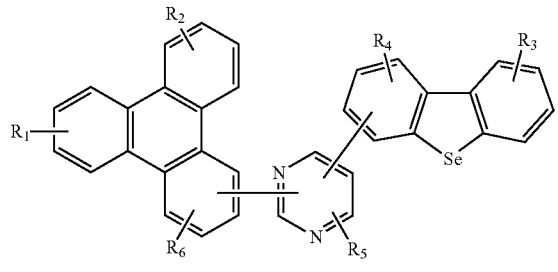
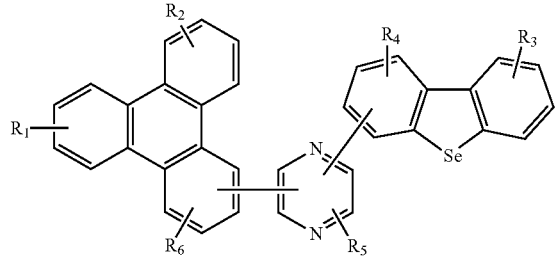
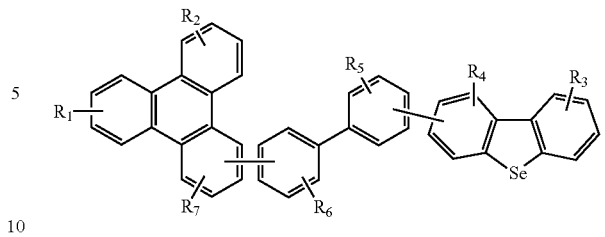
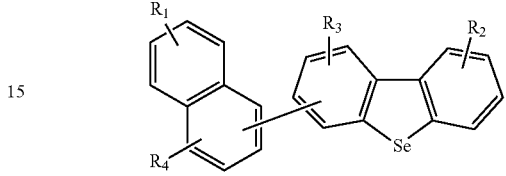
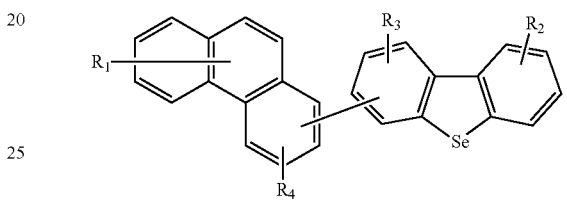
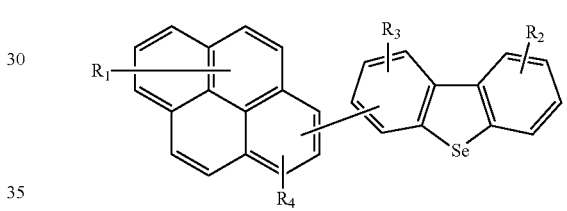
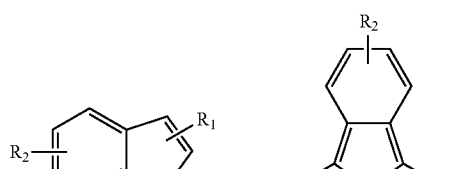
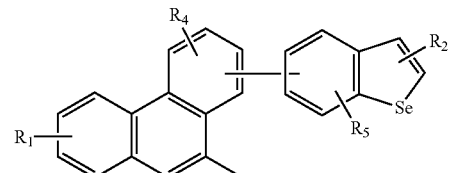
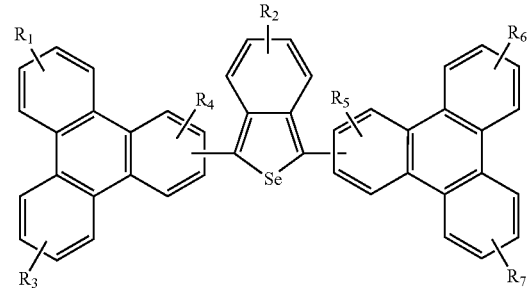

-continued

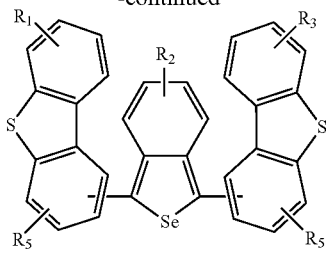

wherein each of $R_1$, $R_2$, $R_3$, $R_4$, $R_5$, $R_6$ and $R_7$ indicates an optional substitutent to any possible position in the relevant moiety, Ar indicates an aromatic group, and each line linking two molecular moieties indicates attachment between the two moieties at any possible positions on the respective moieties. Each $R_1$, $R_2$, $R_3$, $R_4$, $R_5$, $R_6$ and $R_7$ may represent multiple substitutions Suitable substitutents include but are not limited to halo, alkyl, heteroalkyl, cycloalkyl, alkenyl, alkynyl, arylkyl, heterocyclic group, aryl, and heteroaryl. Preferably, the substitutent is selected from the group consisting of heterocyclic group, aryl, aromatic group, and heteroaryl. In one embodiment, the substitutent is an aromatic group, including but not limited to benzene and substituted benzene; polyaromatic group such as benzocyclopropane, benzocyclopropane, benzocyclobutadiene, and benzocyclobutene, naphthalene, anthracene, tetracene, pentacene, phenanthrene, triphenylene, helicenes, corannulene, azulene, acenaphthylene, fluorene, chrysene, fluoranthene, pyrene, benzopyrene, coronene, hexacene, picene, perylene; and heteroaromatic group such as furan, benzofuran, isobenzofuran, pyrrole, indole, isoindole, thiophene, benzothiophene, benzo[c]thiophene, imidazole, benzimidazole, purine, pyrazole, indazole, oxazole, benzoxazole, isoxazole, benzisoxazole, thiazole, benzothiazole, pyridine, quinoline, isoquinoline, pyrazine, quinoxaline, acridine, pyrimidine, quinazoline, pyridazine, cinnoline; and derivatives thereof.

The linkage between two molecular moieties as indicated by the line linking the two molecular moieties can be a single bond or multiple bonds. In one embodiment, the linkage is a single bond between two atoms in respective molecular moieties. In another embodiment, the linkage is via multiple bonds, e.g., via a fused ring.

In another embodiment, the invention provides an organoselenium compound selected from the group consisting of:

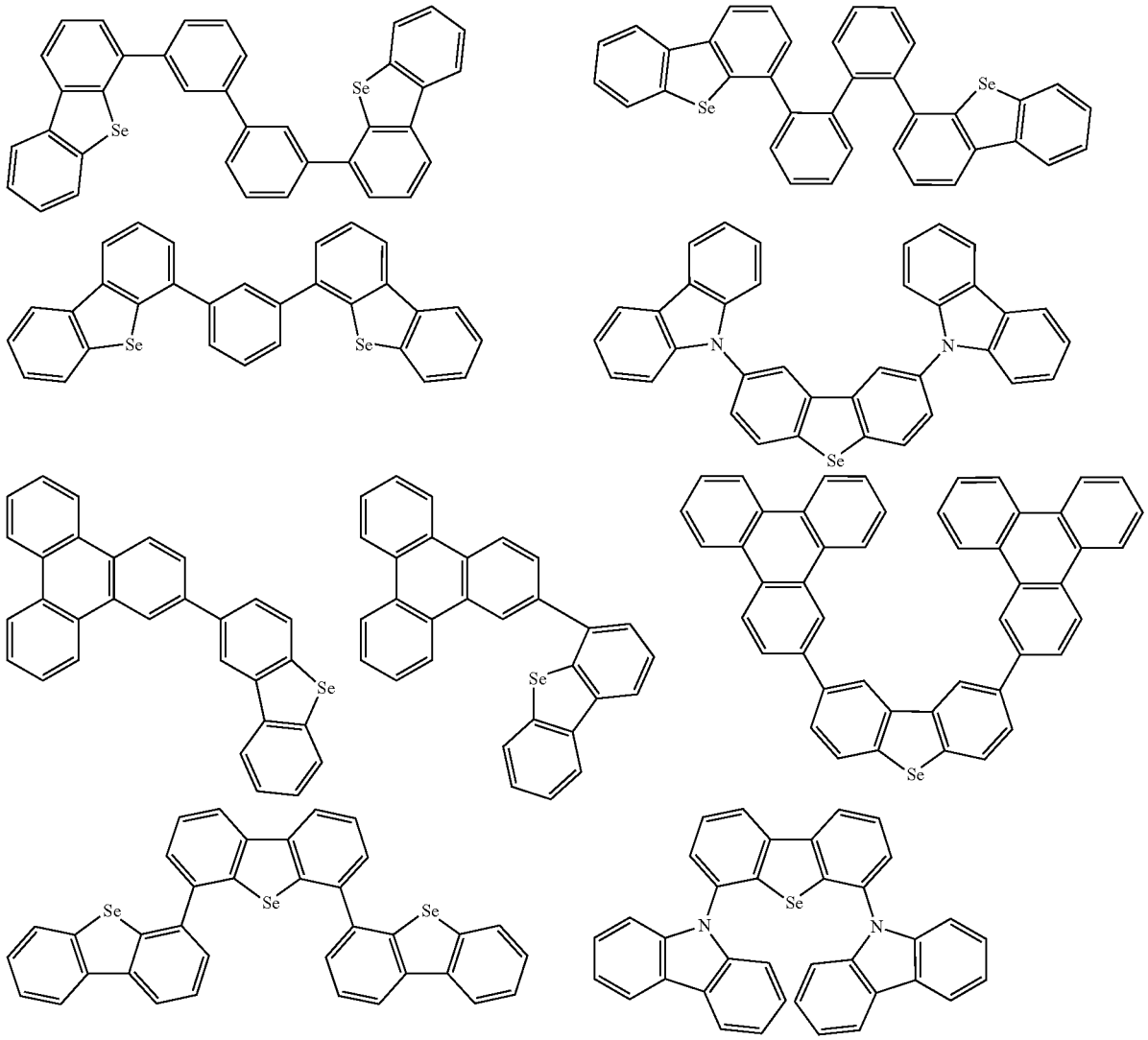

-continued
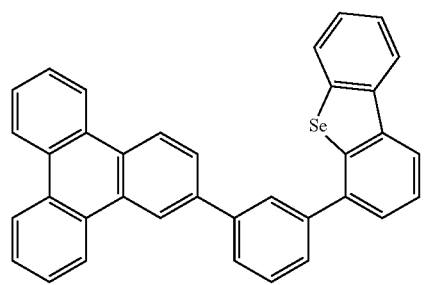
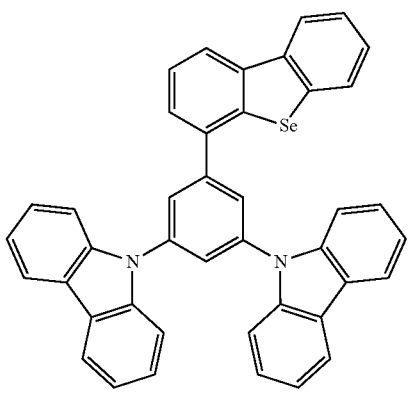
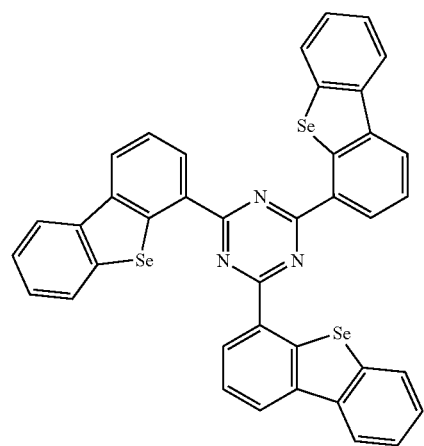
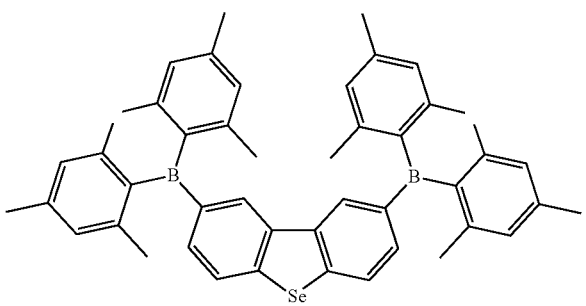
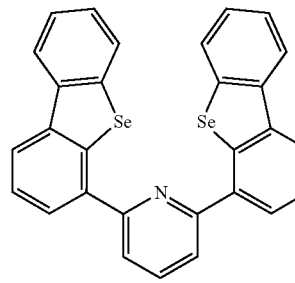
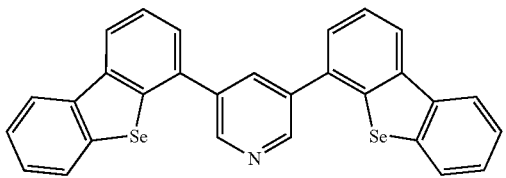
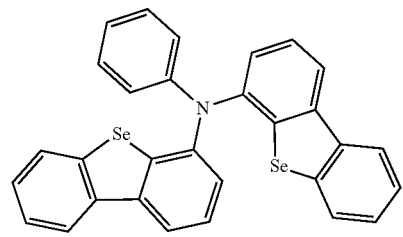
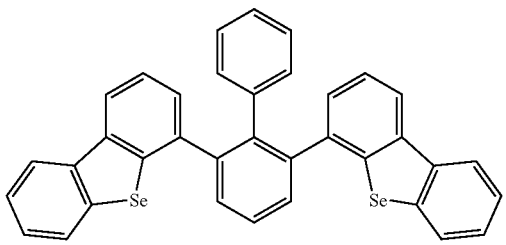
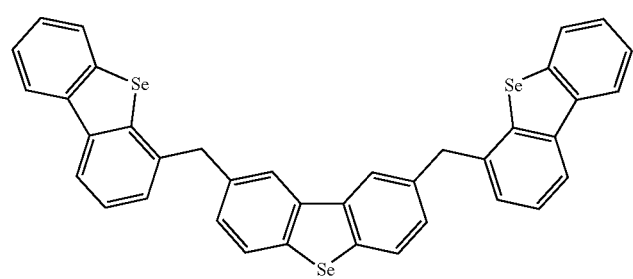

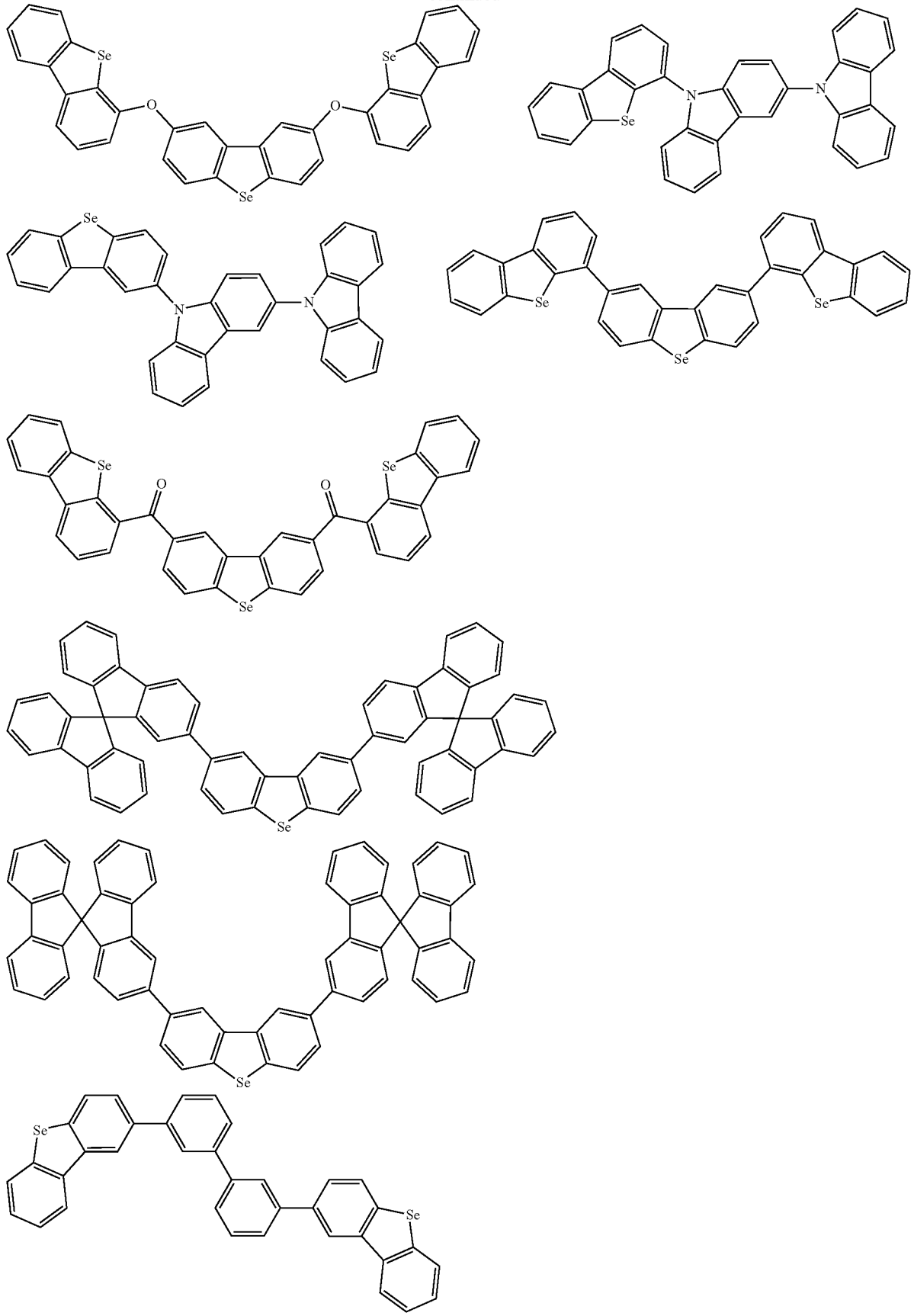

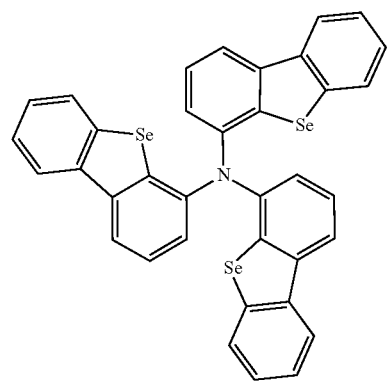
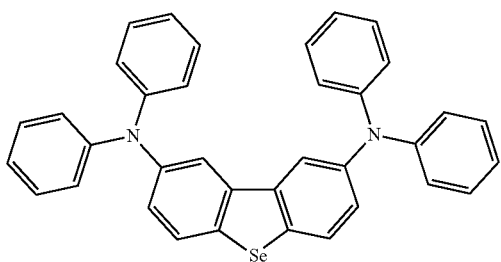
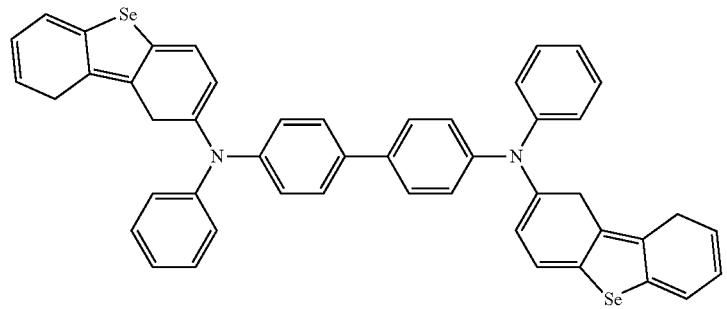
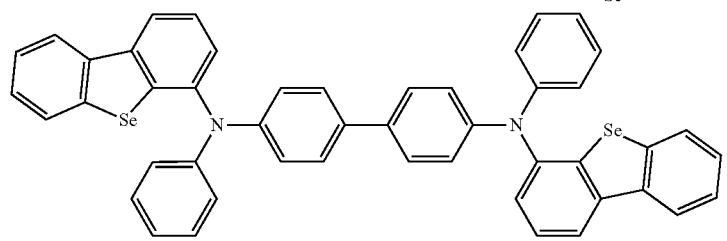
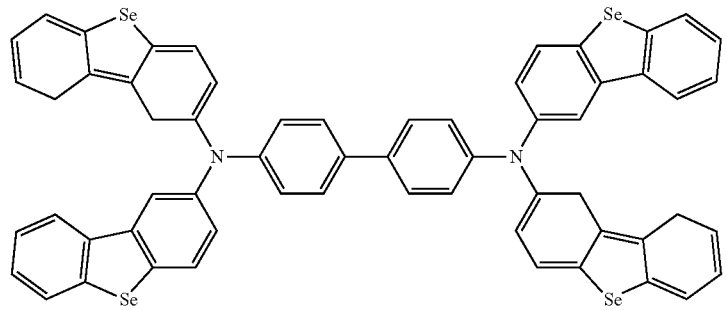
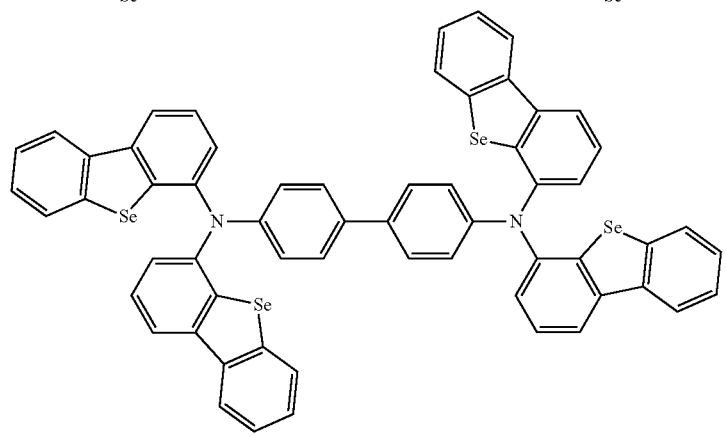

-continued
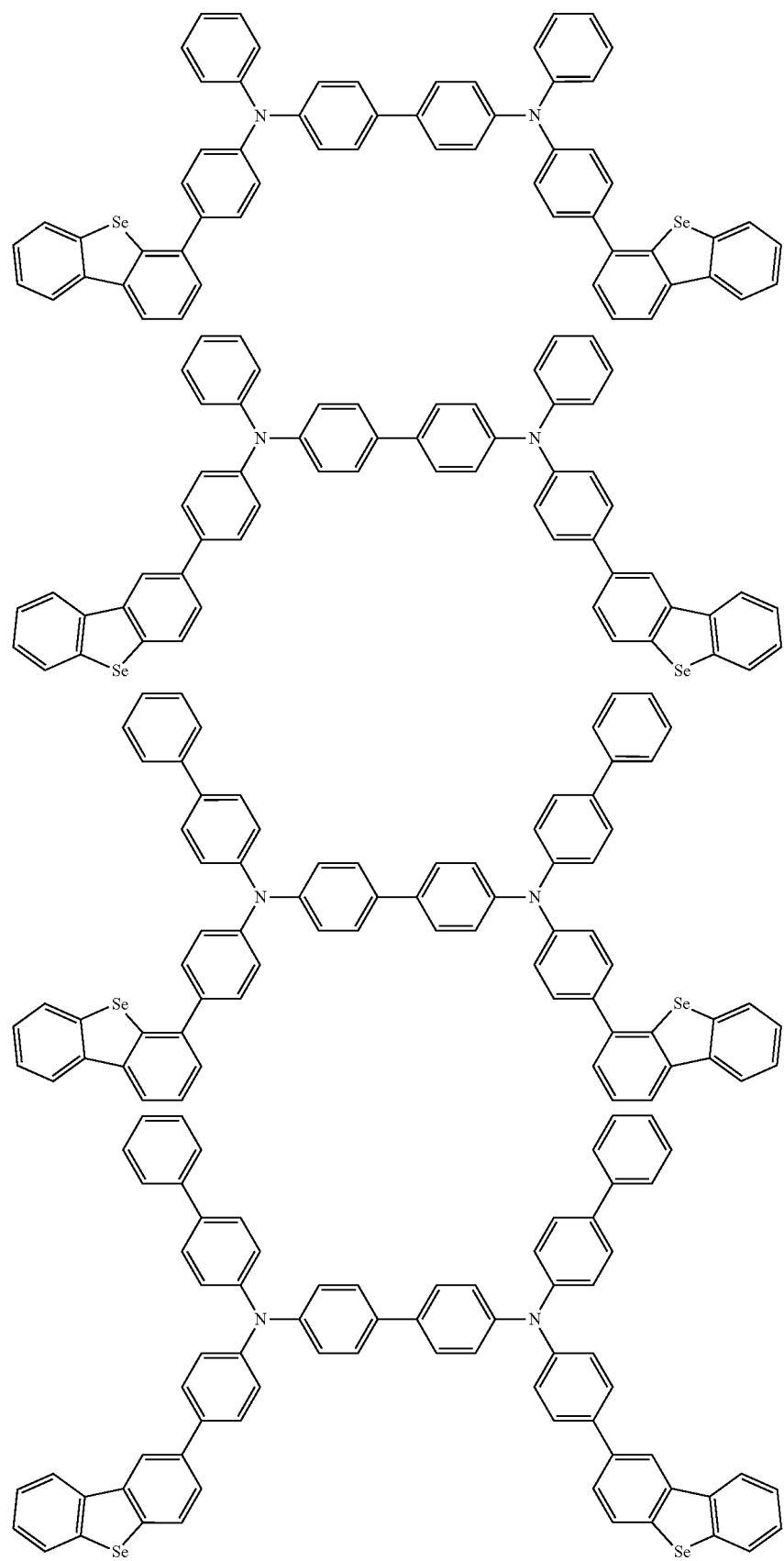

-continued
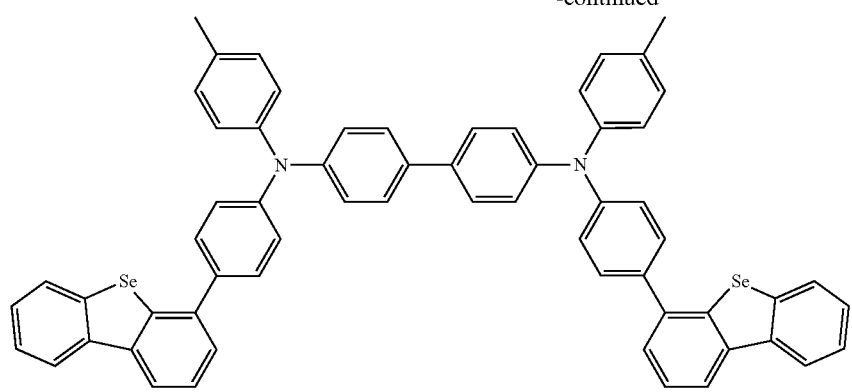
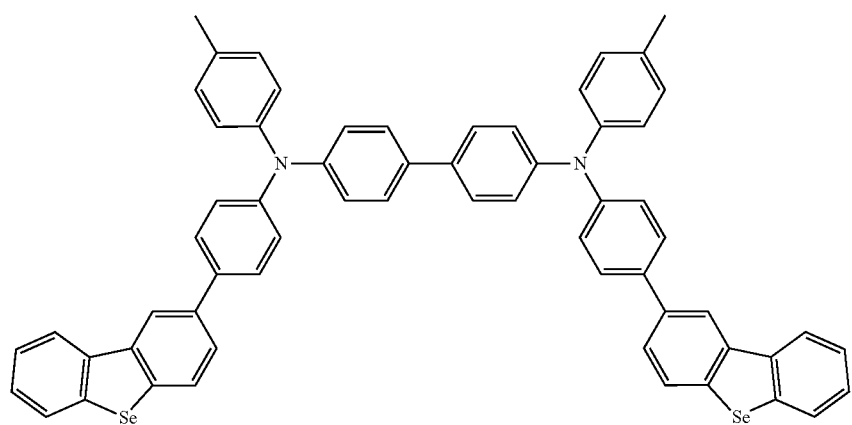
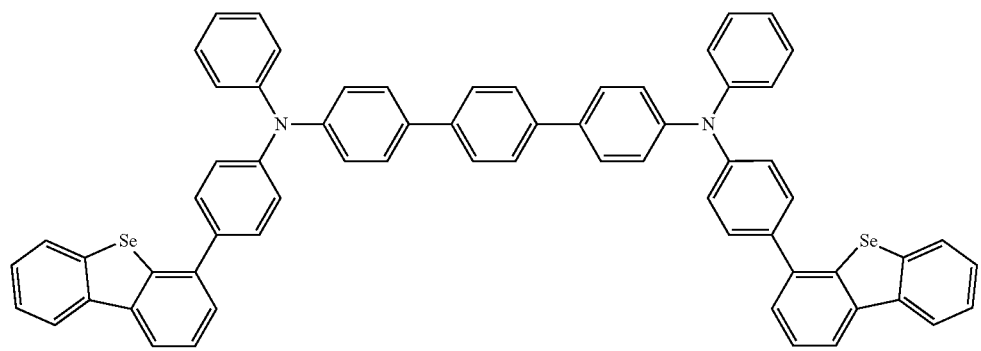
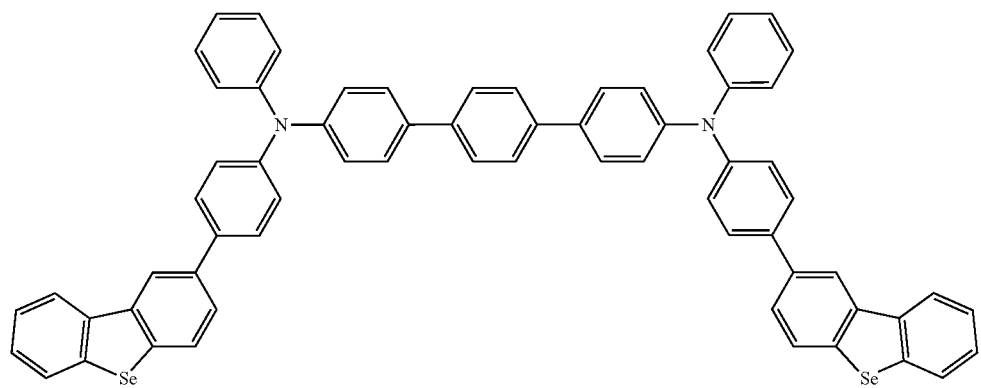

-continued
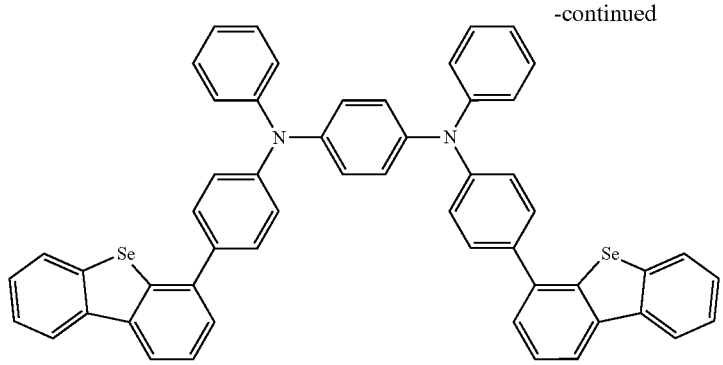
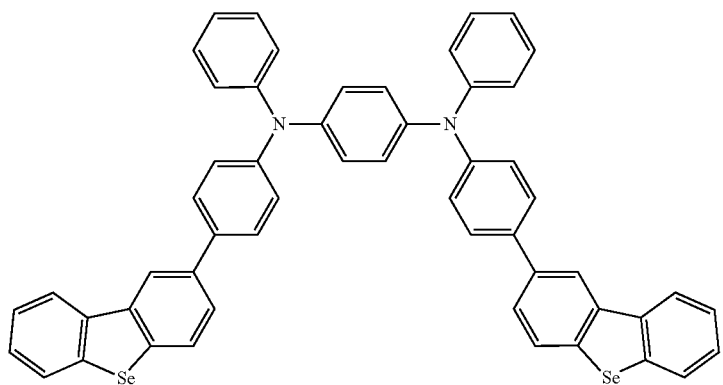
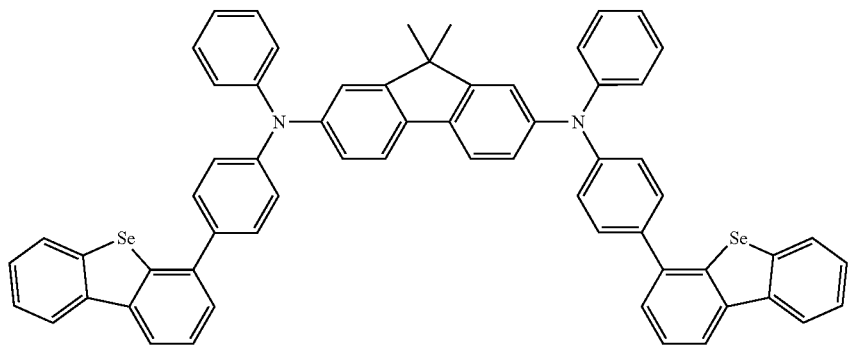
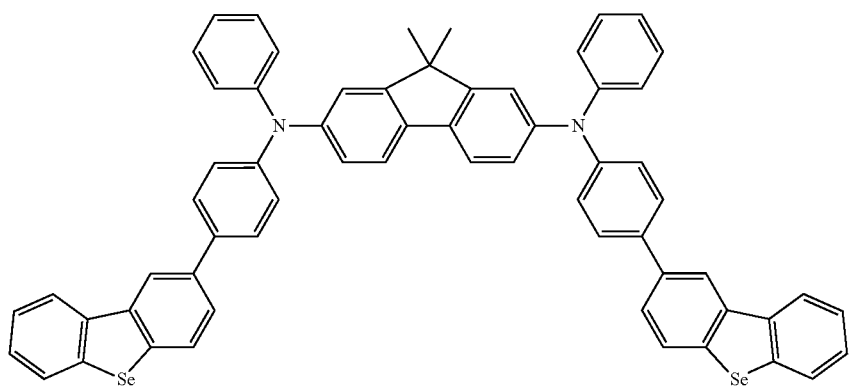

-continued
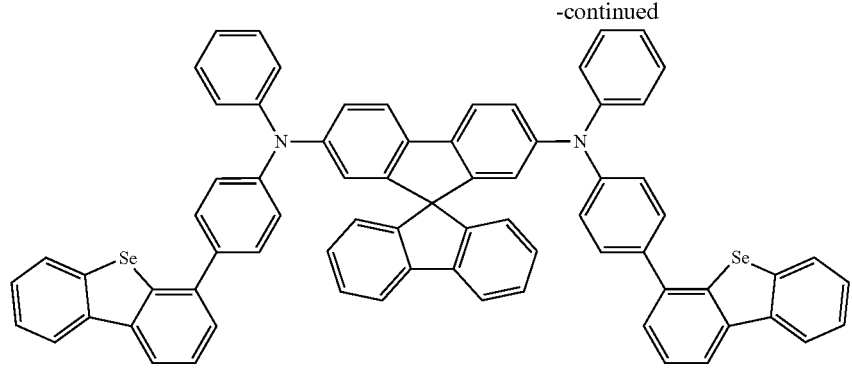
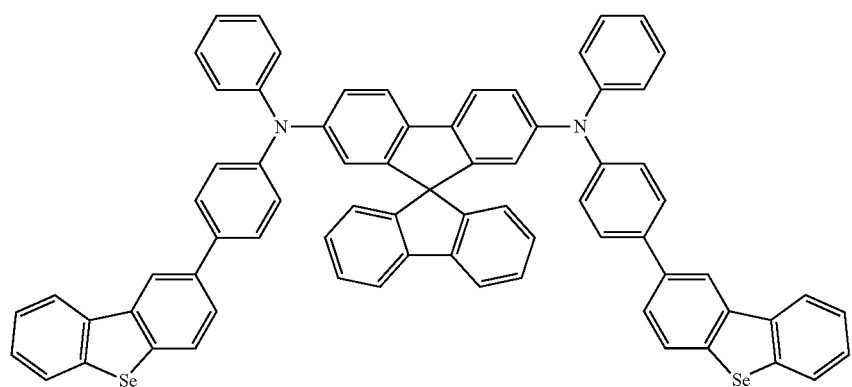
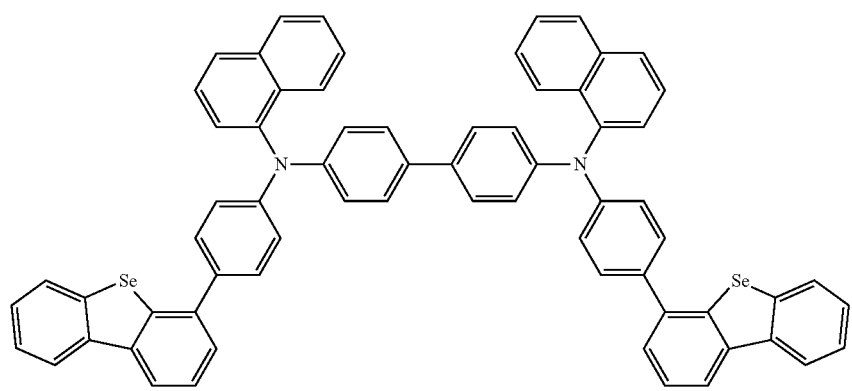
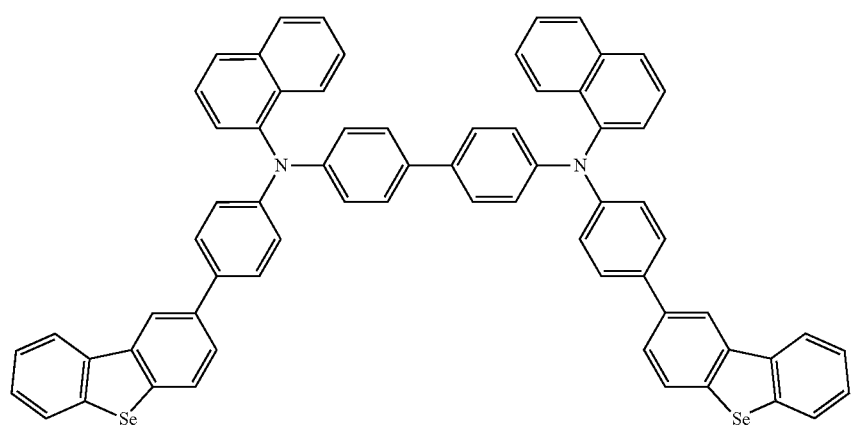

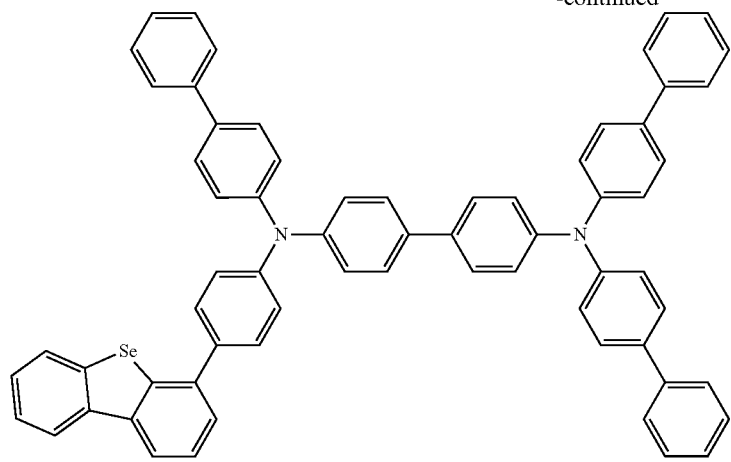
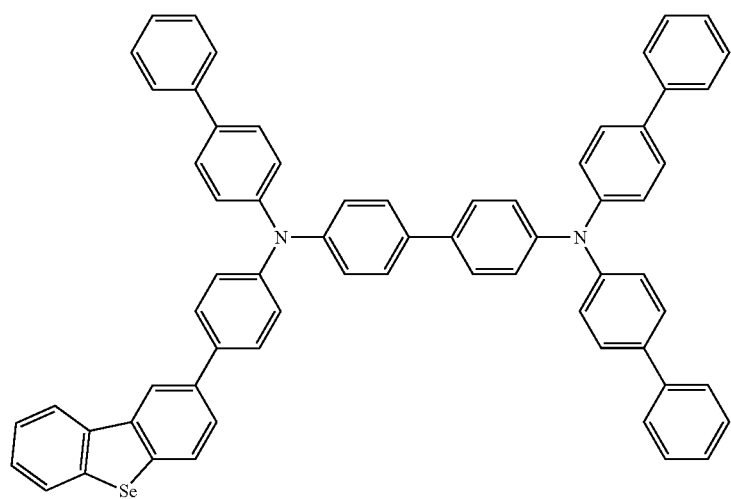
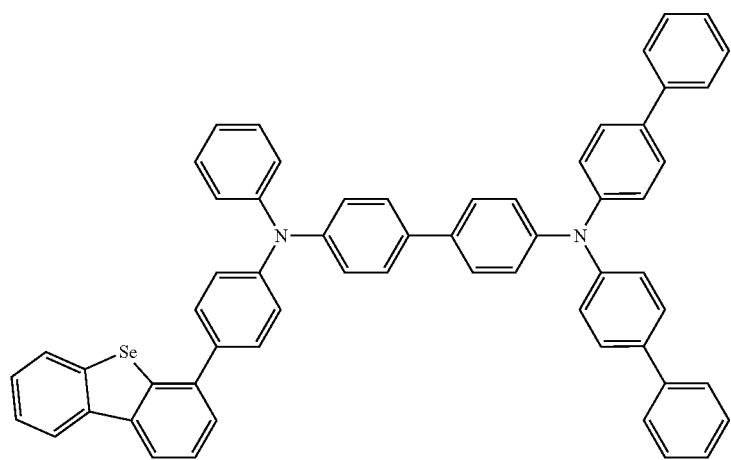

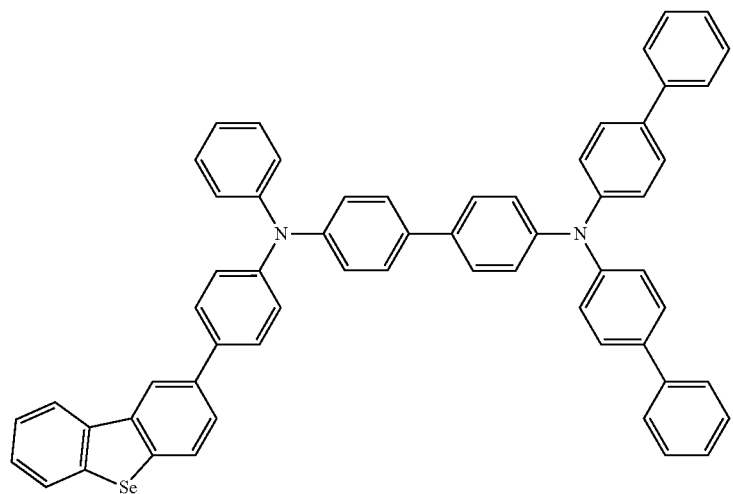
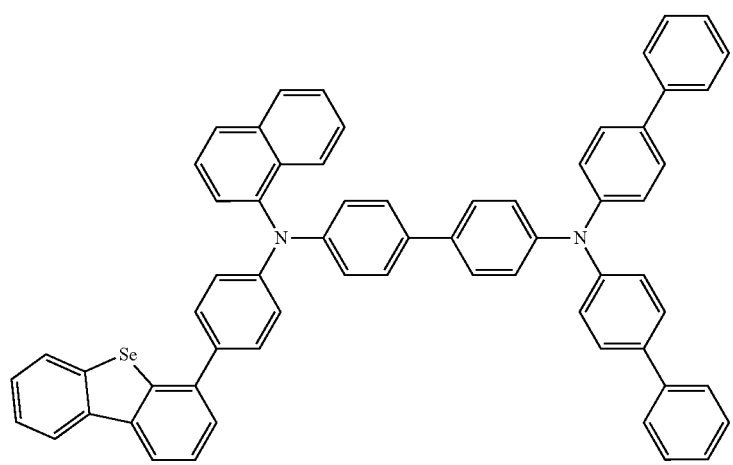
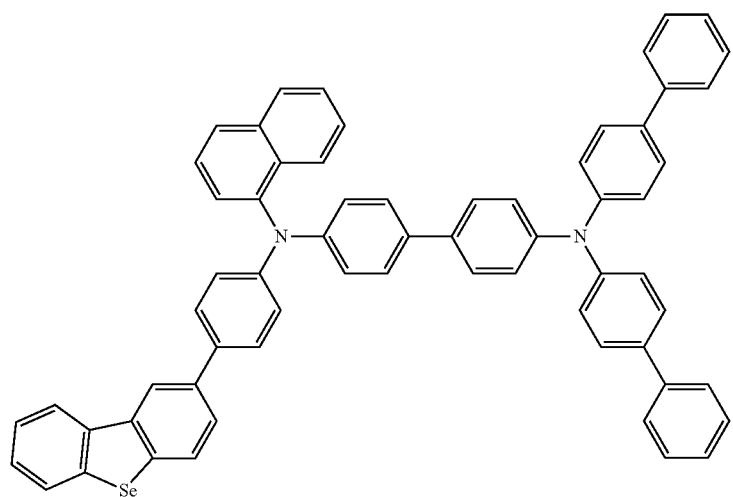

-continued
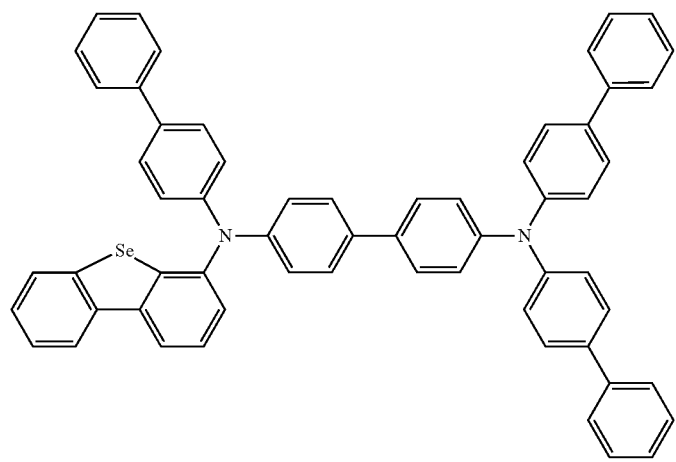
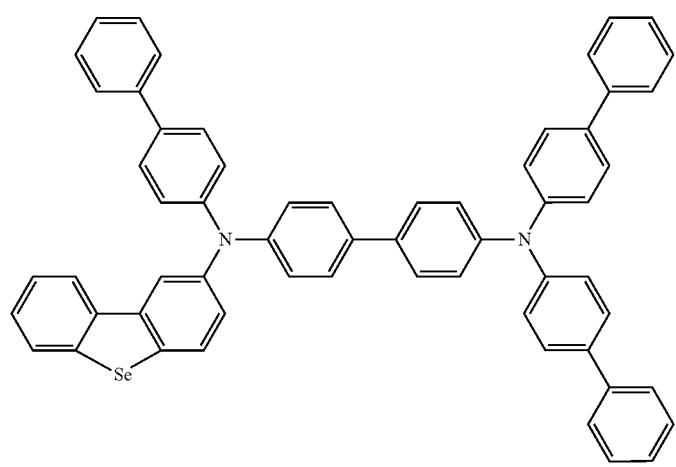
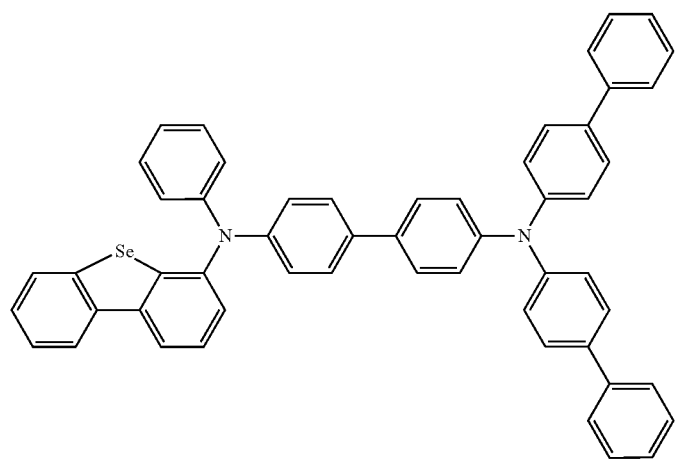

-continued
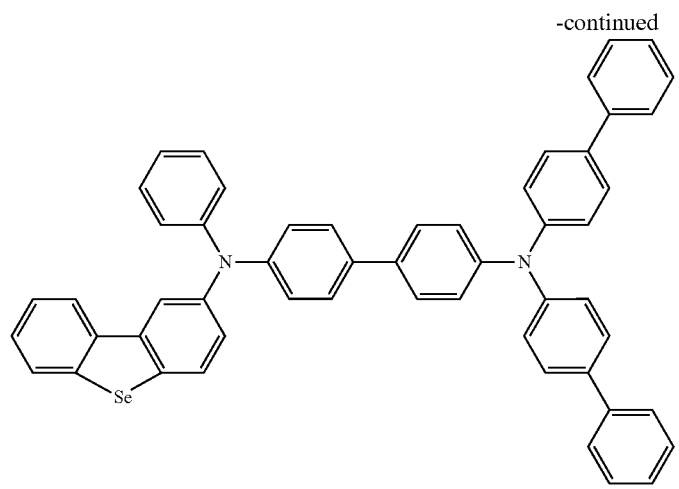
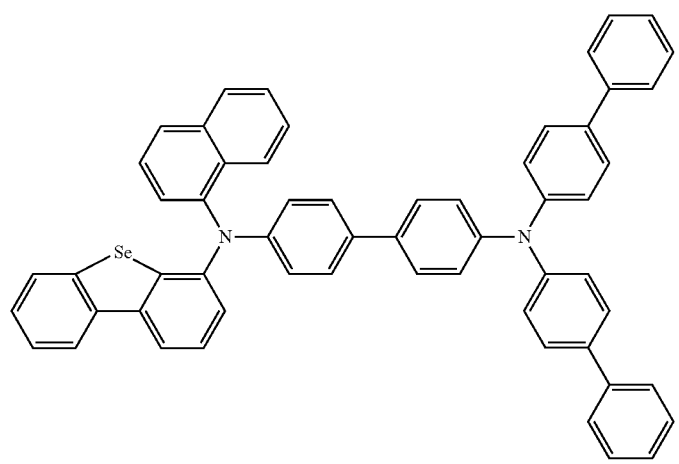
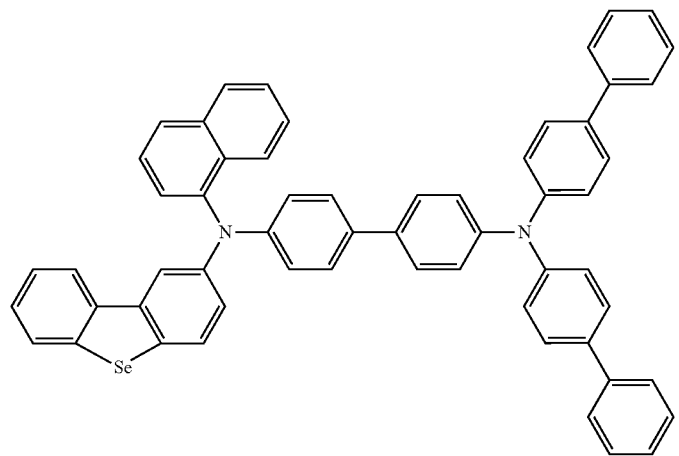

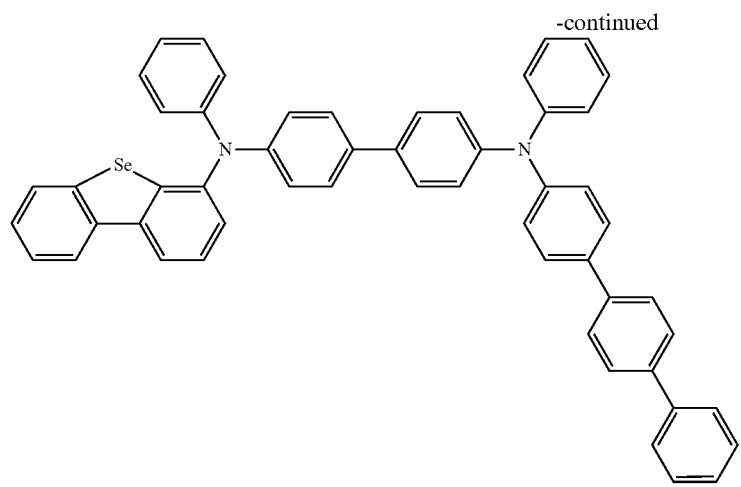
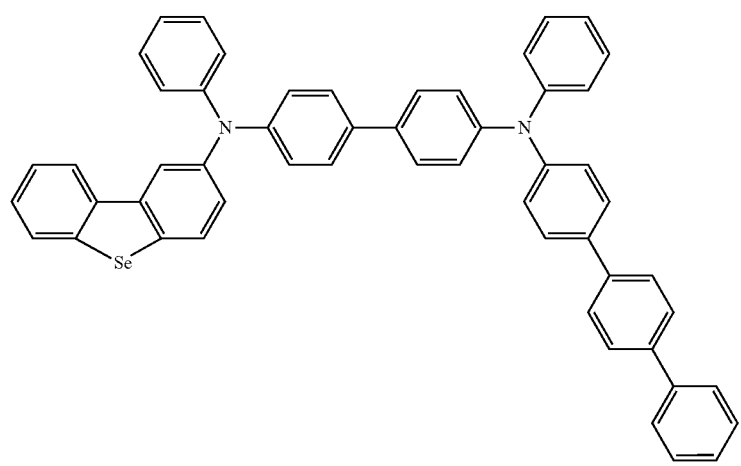
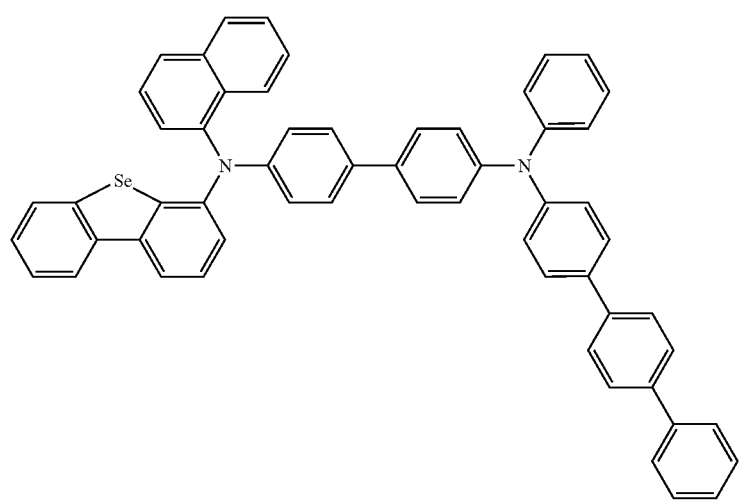

-continued
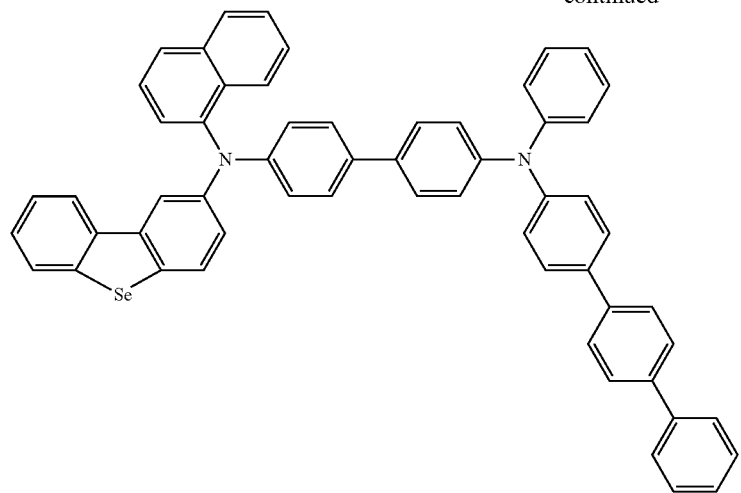
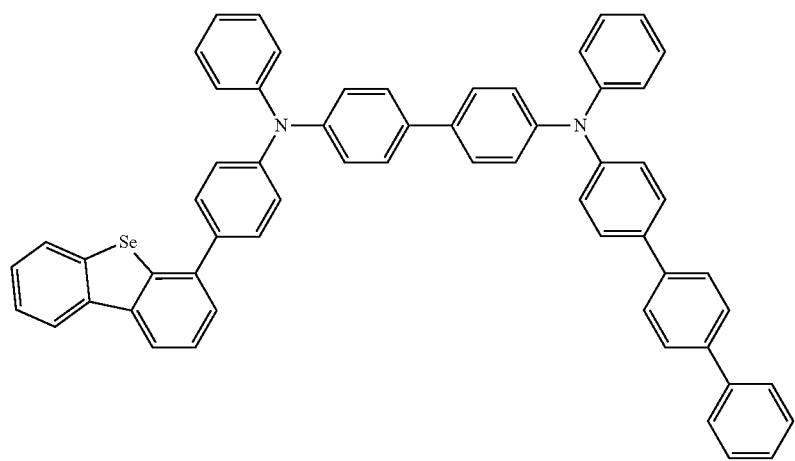
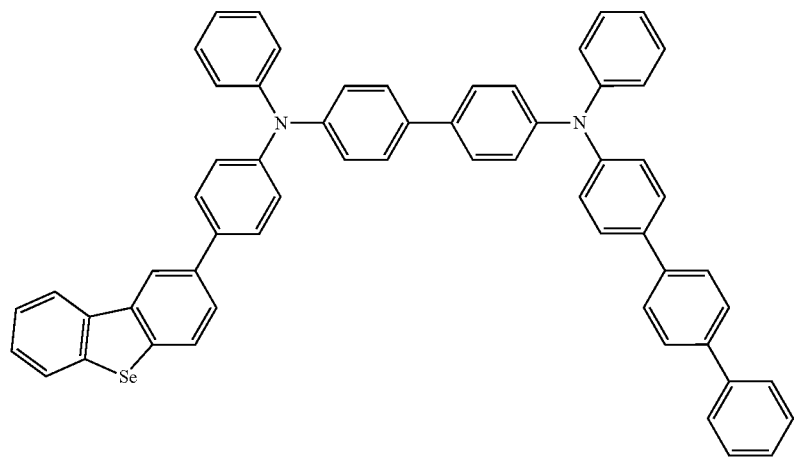

-continued
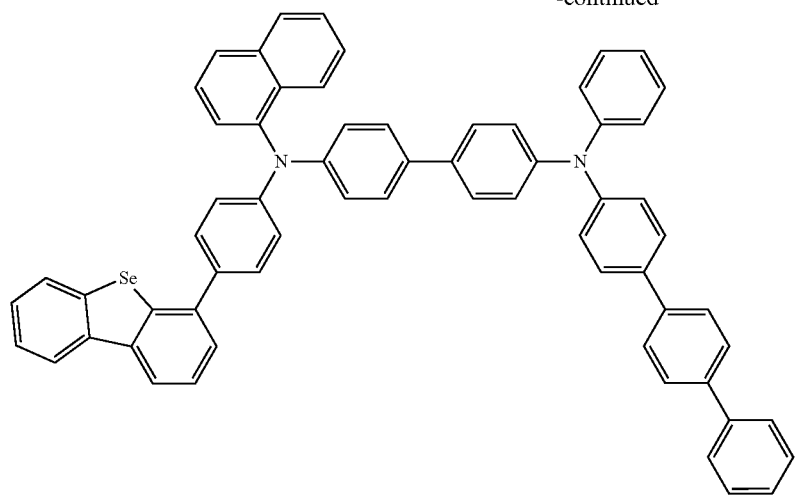
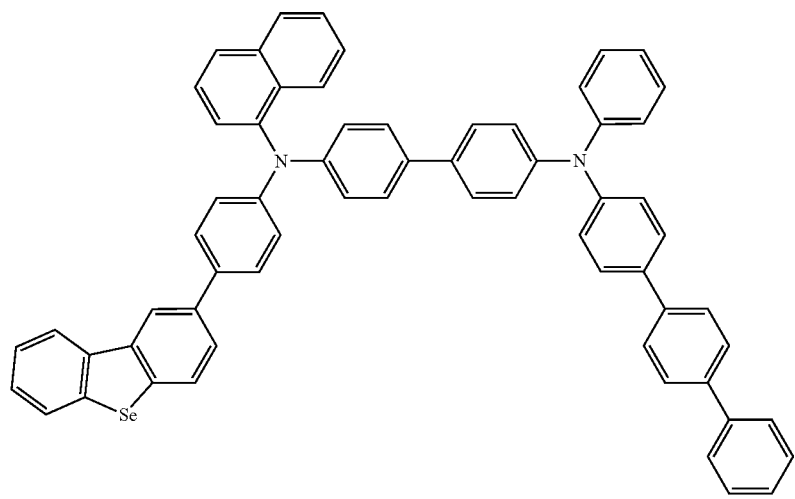
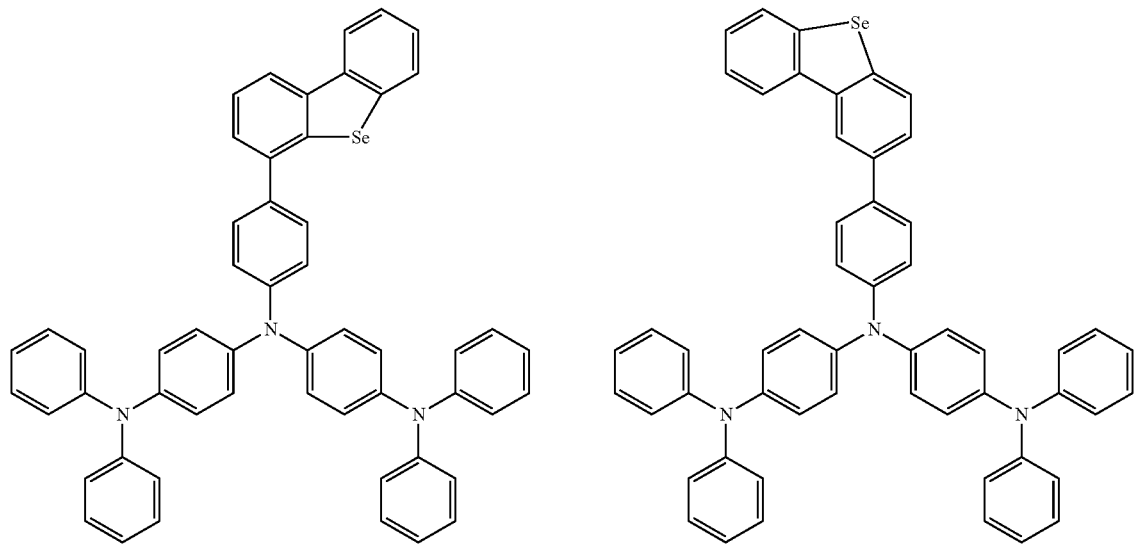

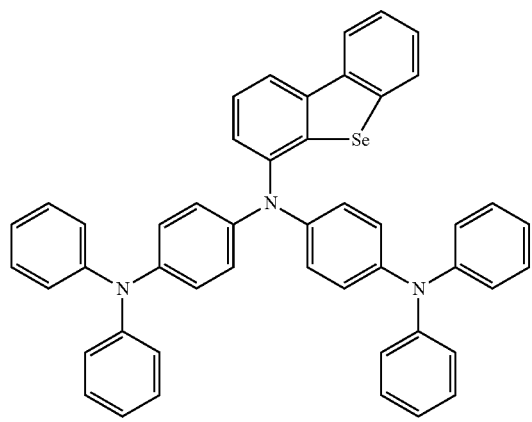
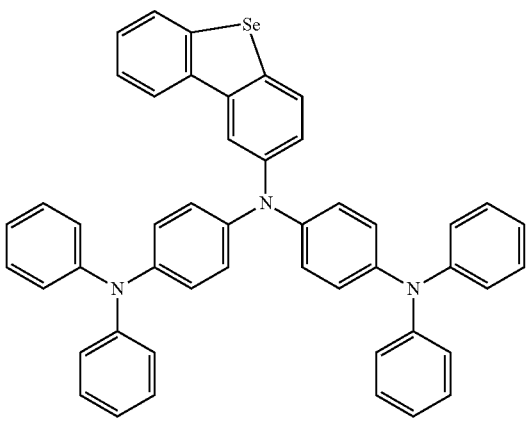
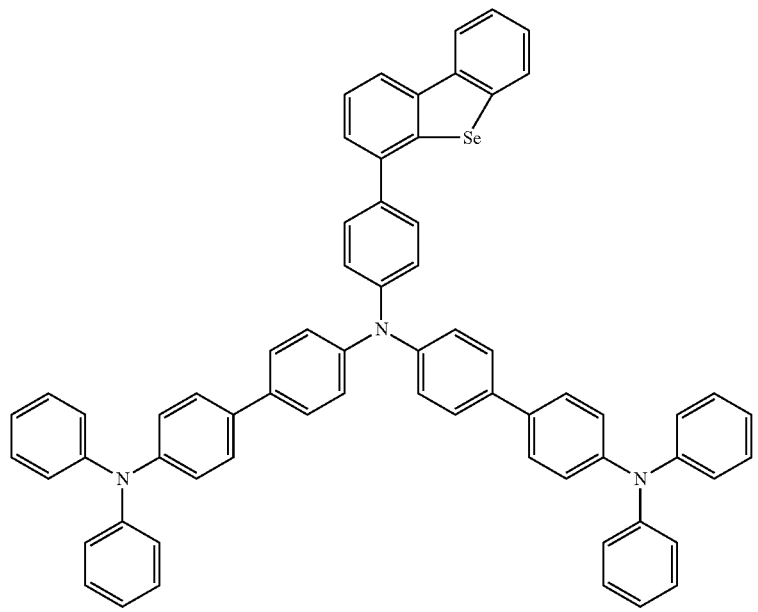
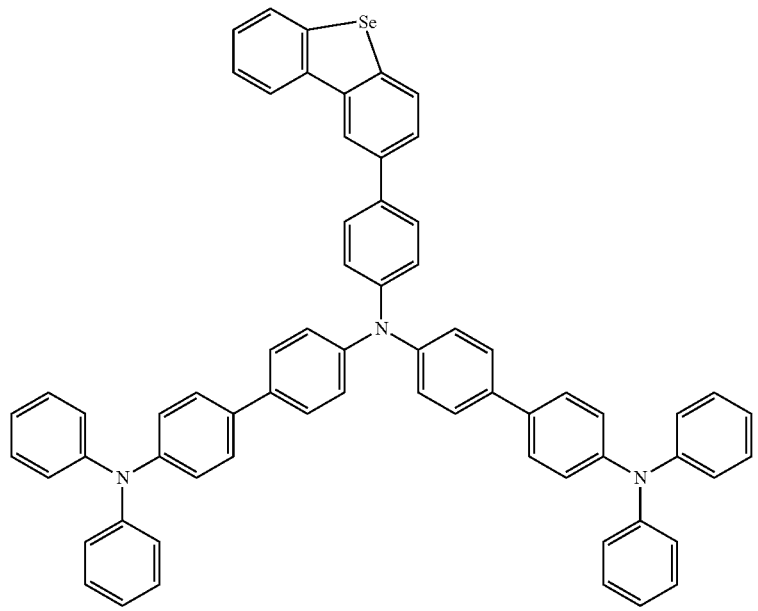

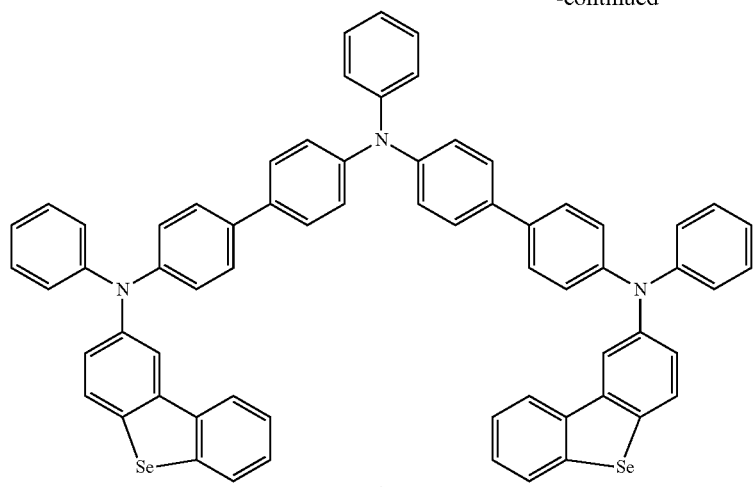

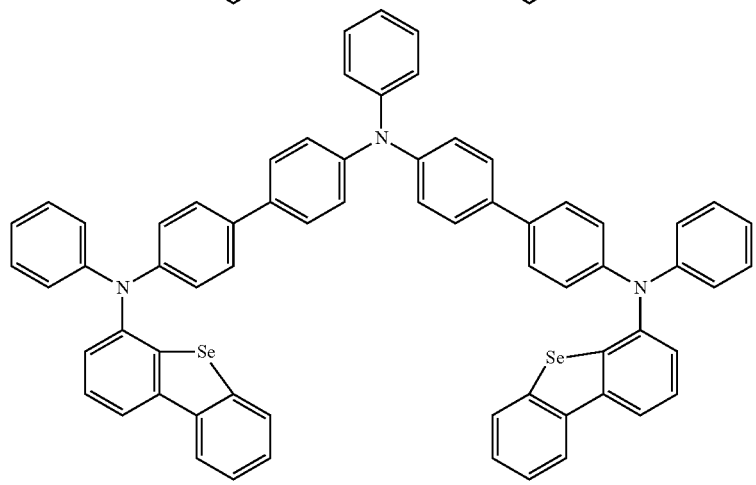

and derivatives thereof. Derivatives, such as compounds substituted by a substitutent, including but not limited to halo, alkyl, heteroalkyl, cycloalkyl, alkenyl, alkynyl, arylkyl, heterocyclic group, aryl, and heteroaryl, are contemplated.

In one embodiment, organoselenium compound is

H-1

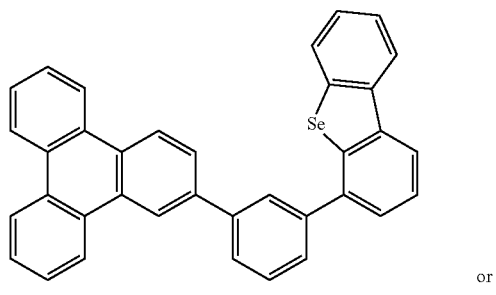

or

H-2

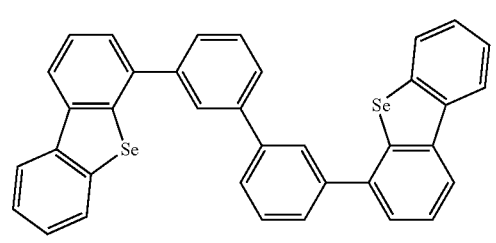

or a derivative thereof, such as such as the compound substituted by a substitutent, including but not limited to halo, alkyl, heteroalkyl, cycloalkyl, alkenyl, alkynyl, arylkyl, heterocyclic group, aryl, and heteroaryl.

In still another embodiment, the organoselenium compound is selected from the group consisting of:

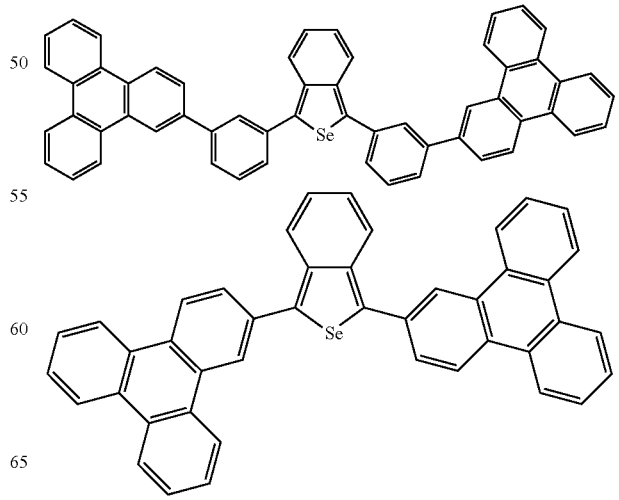

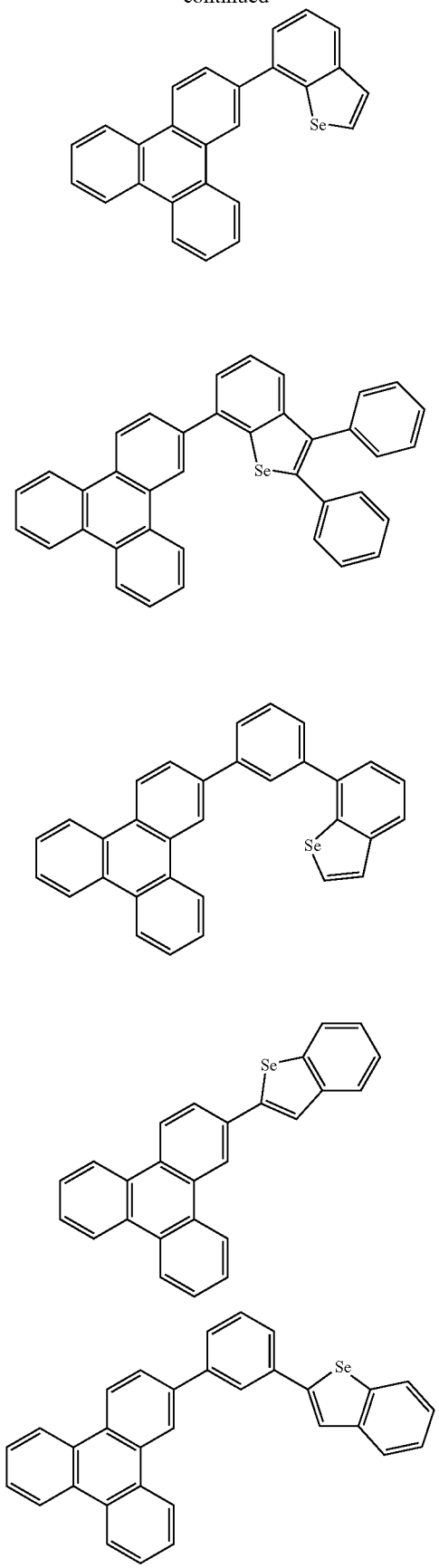

and derivatives thereof. Derivatives, such compounds substituted by a substitutent, including but not limited to halo, alkyl, heteroalkyl, cycloalkyl, alkenyl, alkynyl, arylkyl, heterocyclic group, aryl, and heteroaryl, are contemplated.

The organoselenium compounds of the present invention can be prepared by methods known in the art, including but not limited to method illustrated in the Examples below.

An organic light emitting device comprising the organoselenium compound of the invention is also provided. The device may include an anode, a cathode, and an organic emissive layer disposed between the anode and the cathode. The organic emissive layer may include a host and a phosphorescent dopant. In one embodiment, the device includes the organoselenium material of the invention as the host material in an emissive layer. Any of the dopants listed in Table 1 below may be used in the emissive layer in conjunction with an organoselenium material as the host material. In a preferred embodiment, the dopant is a red dopant selected from the list of red dopants in Table 1. In another preferred embodiment, the dopant is a green dopant selected from the list of green dopants in Table 1. In still another embodiment, the dopant is a blue dopant selected from the list of blue dopants in Table 1.

The concentration of the dopant in the emissive layer can be determined by a person skilled in the art based on the particular dopant used and the requirement of the device.

The organic light emitting device may comprise additionally a hole transporting layer (HTL) or an electron transporting layer (ETL). In preferred embodiments, the hole transporting layer or the electron transporting layer comprises an organoselenium material of the invention.

Combination with Other Materials

The organoselenium materials described herein as useful for a particular layer in an organic light emitting device may be used in combination with a wide variety of other materials present in the device. For example, the organoselenium material of the invention can be used as a host of an emissive layer in conjunction with one or more emissive dopants disclosed in Table 1.

The organoselenium material may also be used in conjunction with a wide variety of other host materials disclosed in Table 1 in transport layers, blocking layers, injection layers, electrodes and other layers that may be present in an OLED.

The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
| --- | --- | --- |
| Hole injection materials | | |
| Phthalocyanine and porphyrin compounds | | Appl. Phys. Lett. 69, 2160 (1996) |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | | Synth. Met. 87, 171 (1997) WO2007002683 |
| Phosphonic acid and silane SAMs | | US20030162053 |

TABLE 1-continued
| MATERIAL | EXAMPLES OF MATERIAL | PUBLICATIONS |
|---|---|---|
| Triarylamine or polythiophene polymers with conductivity dopants | 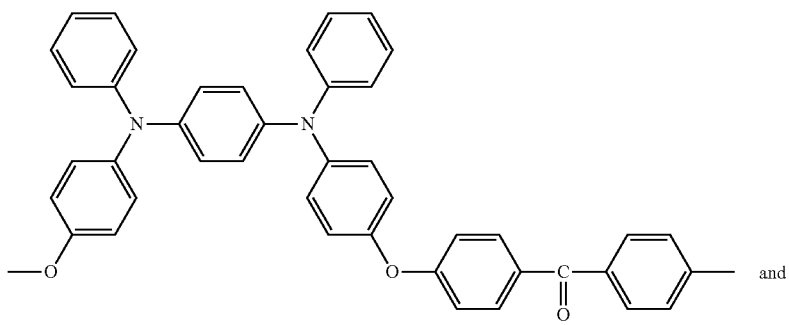 | EA01725079A1 |
| Arylamines complexed with metal oxides such as molybdenum and tungsten oxides | 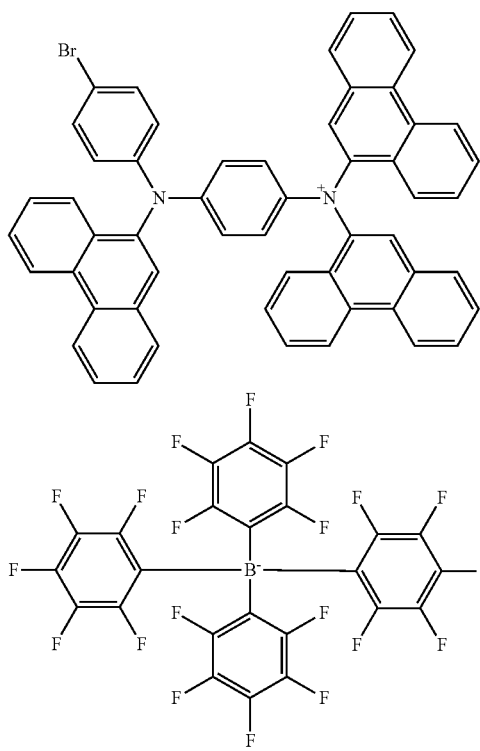 | SID Symposium Digest, 37, 923 (2006)<br>WO2009018009 |
| p-type semiconducting organic complexes | 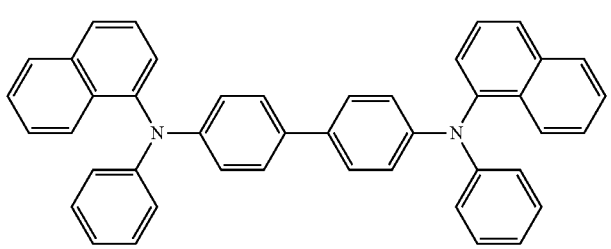 [SMILES: c1ccc(N(c2ccc(-c3ccc(N(c4ccccc4)c4cccc5ccccc45)cc3)cc2)c2cccc3ccccc23)cc1] | US20020158242 |

TABLE 1-continued

| MATERIAL | EXAMPLES OF MATERIAL | PUBLICATIONS |
| --- | --- | --- |
| Metal organometallic complexes | | US20060240279 |
| Cross-linkable compounds | | US20080220265 |
| Hole transporting materials | | |
| Triarylamines (e.g., TPD, α-NPD) | | Appl. Phys. Lett. 51, 913 (1987) |
| | | US5061569 |

TABLE 1-continued
| MATERIAL | EXAMPLES OF MATERIAL | PUBLICATIONS |
|---|---|---|
| | 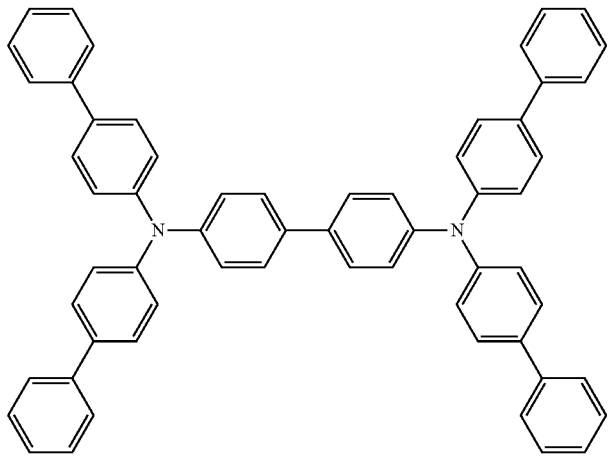 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 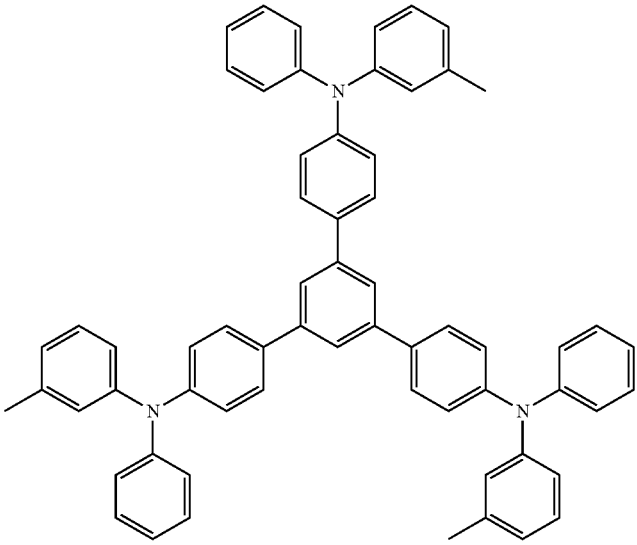 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 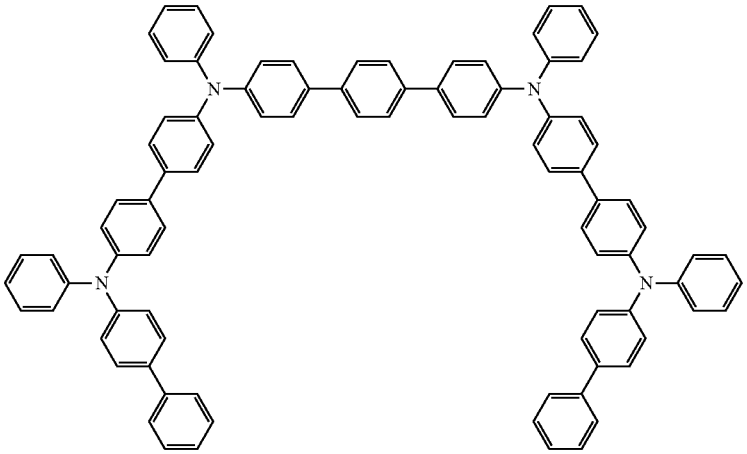 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 1-continued

| MATERIAL | EXAMPLES OF MATERIAL | PUBLICATIONS |
|---|---|---|
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 |

TABLE 1-continued

| MATERIAL | EXAMPLES OF MATERIAL | PUBLICATIONS |
| --- | --- | --- |
| Indolocarbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |

TABLE 1-continued
| MATERIAL | EXAMPLES OF MATERIAL | PUBLICATIONS |
|---|---|---|
| Metal 8-hydroxyquinolates (e.g., Alq$_3$, BAlq) | 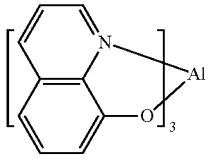 | Nature 395, 151 (1998) |
| | 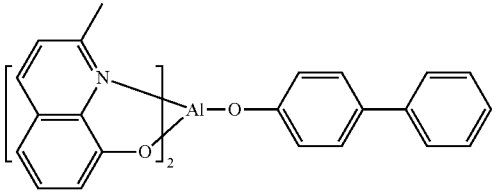 | US20060202194 |
| | 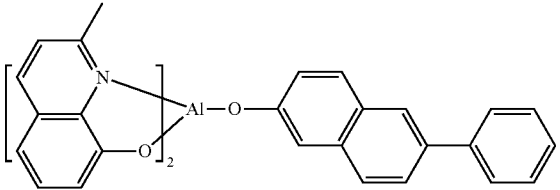 | WO2005014551 |
| | 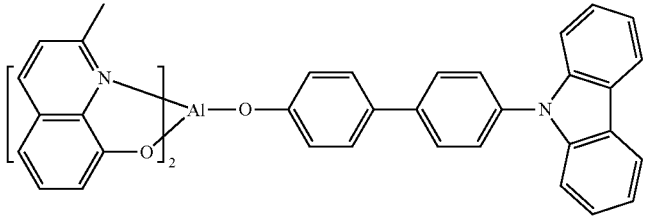 | WO2006072002 |
| Metal phenoxybenzothiazole compounds | 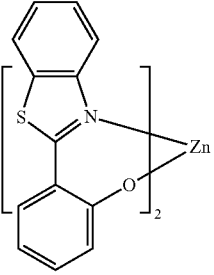 | Appl. Phys. Lett. 90, 123509 (2007) |
| Conjugated oligomers and polymers (e.g., polyfluorene) | 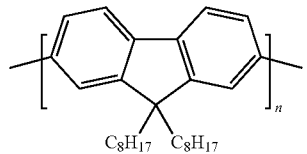 | Org. Electron. 1, 15 (2000) |
| Aromatic fused rings | 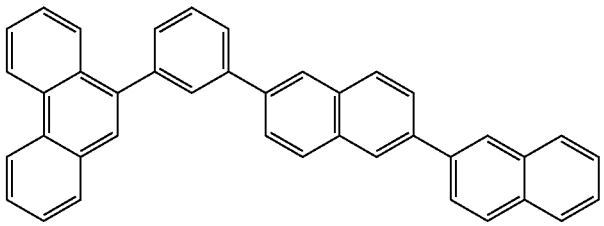 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |

TABLE 1-continued

| MATERIAL | EXAMPLES OF MATERIAL | PUBLICATIONS |
| --- | --- | --- |
| Zinc complexes | | WO2009062578 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

| MATERIAL | EXAMPLES OF MATERIAL | PUBLICATIONS |
|---|---|---|
| | 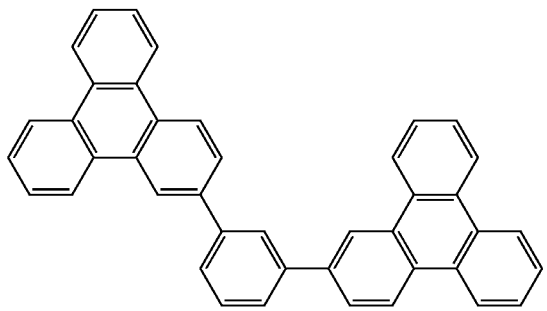 [SMILES: c1cc(-c2ccc3c4ccccc4c4ccccc4c3c2)cc(-c2ccc3c4ccccc4c4ccccc4c3c2)c1] | US20060280965 |
| | 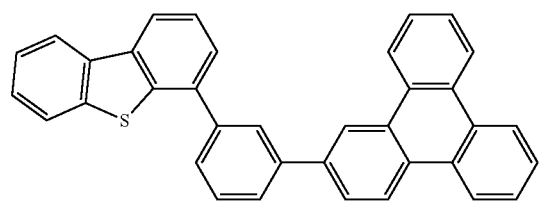 [SMILES: c1cc(-c2ccc3c4ccccc4c4ccccc4c3c2)cc(-c2cccc3c2sc2ccccc23)c1] | WO2009021126 |
| Donor acceptor type molecules | 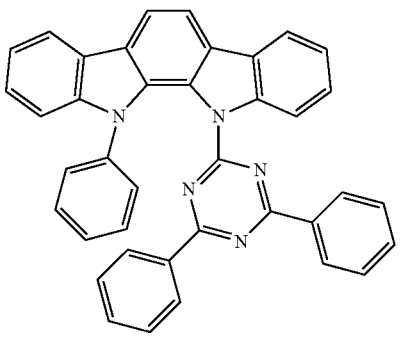 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/DBT/ DBF | 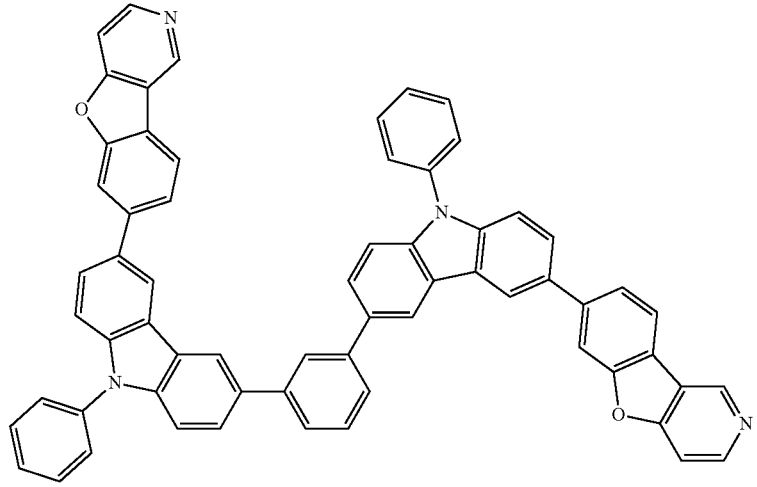 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 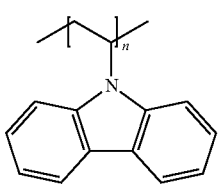 | Appl. Phys. Lett. 77, 2280 (2000) |

TABLE 1-continued

| MATERIAL | EXAMPLES OF MATERIAL | PUBLICATIONS |
|---|---|---|
| Spirofluorene compounds | | WO2004093207 |
| Metal phenoxybenzooxazole compounds | | WO2005089025 |
| | | WO2006132173 |
| | | JP200511610 |
| Spirofluorene-carbazole compounds | | JP2007254297 |

TABLE 1-continued
| MATERIAL | EXAMPLES OF MATERIAL | PUBLICATIONS |
|---|---|---|
|  | 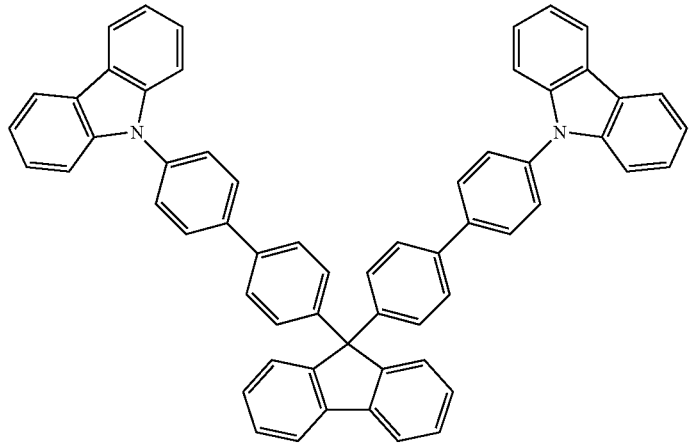 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocarbazoles | 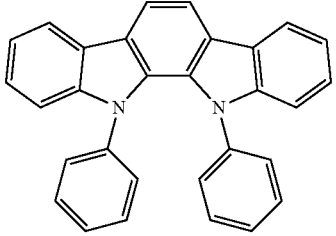 [SMILES: c1ccc(-n2c3ccccc3c3ccc4c5ccccc5n(-c5ccccc5)c4c32)cc1] | WO2007063796 |
|  | 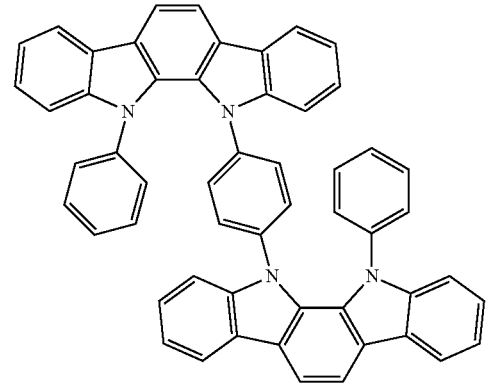 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 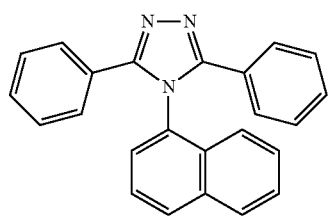 [SMILES: c1ccc(-c2nnc(-c3ccccc3)n2-c2cccc3ccccc23)cc1] | J. Appl. Phys. 90, 5048 (2001) |
|  | 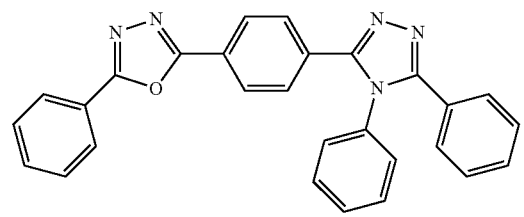 [SMILES: c1ccc(-c2nnc(-c3ccc(-c4nnc(-c5ccccc5)n4-c4ccccc4)cc3)o2)cc1] | WO2004107822 |

TABLE 1-continued
| MATERIAL | EXAMPLES OF MATERIAL | PUBLICATIONS |
|---|---|---|
| Tetraphenylene complexes | 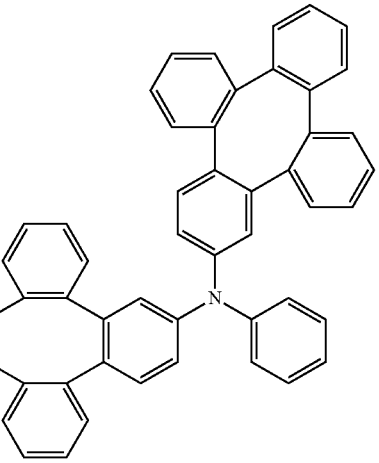 | US20050112407 |
| Metal phenoxypyridine compounds | 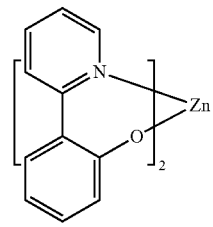 | WO2005030900 |
| Metal coordination complexes (e.g., Zn, Al with N^N ligands) | 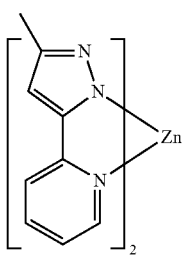 | US20040137268, US20040137267 |
Blue hosts
| | | |
|---|---|---|
| Arylcarbazoles | 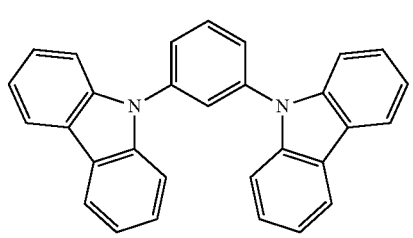 [SMILES: c1cc(-n2c3ccccc3c3ccccc32)cc(-n2c3ccccc3c3ccccc32)c1] | Appl. Phys. Lett, 82, 2422 (2003) |
| | 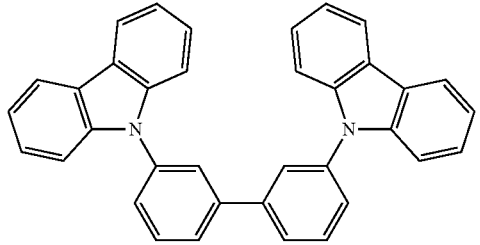 [SMILES: c1cc(-c2cccc(-n3c4ccccc4c4ccccc43)c2)cc(-n2c3ccccc3c3ccccc32)c1] | US20070190359 |

| MATERIAL | EXAMPLES OF MATERIAL | PUBLICATIONS |
|---|---|---|
| Dibenzothiophene/ Dibenzofuran-carbazole compounds | 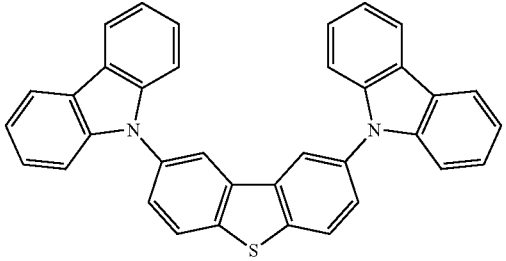 [SMILES: c1ccc2c(c1)c1ccccc1n2-c1ccc2sc3ccc(-n4c5ccccc5c5ccccc54)cc3c2c1] | WO2006114966, US20090167162 |
| | 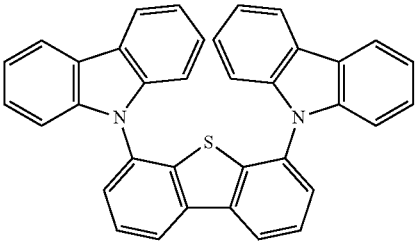 [SMILES: c1cc(-n2c3ccccc3c3ccccc32)c2sc3c(-n4c5ccccc5c5ccccc54)cccc3c2c1] | US20090167162 |
| | 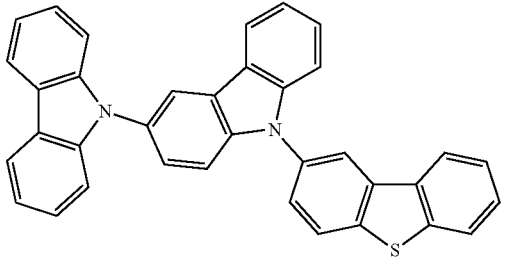 [SMILES: c1ccc2c(c1)sc1ccc(-n3c4ccccc4c4cc(-n5c6ccccc6c6ccccc65)ccc43)cc12] | WO2009086028 |
| | 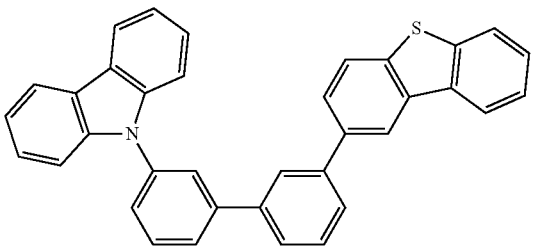 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 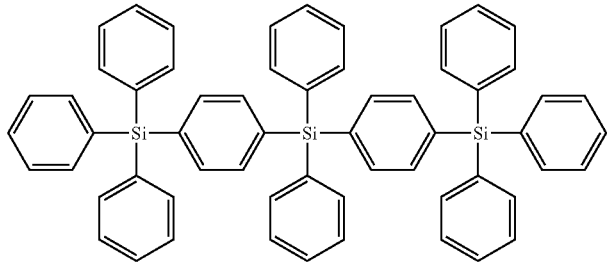 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 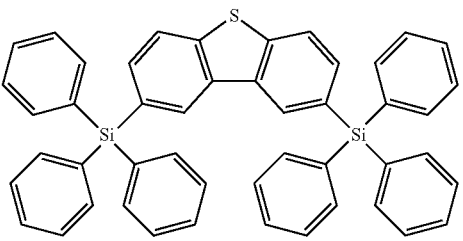 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 1-continued

| MATERIAL | EXAMPLES OF MATERIAL | PUBLICATIONS |
|---|---|---|
| Silicon/Germanium aryl compounds | | EP2034538A |
| Aryl benzoyl ester | | WO2006100298 |
| High triplet metal organometallic complex | | US7154114 |

Phosphorescent dopants

Red dopants

| | | |
|---|---|---|
| Heavy metal porphyrins (e.g., PtOEP) | | Nature 395, 151 (1998) |
| Iridium(III) organometallic complexes | | Appl. Phys. Lett. 78, 1622 (2001) |

TABLE 1-continued

| MATERIAL | EXAMPLES OF MATERIAL | PUBLICATIONS |
|---|---|---|
| | (isoquinoline-phenyl)₂Ir(acac) structure | US2006835469 |
| | (methyl-quinoline-phenyl)₂Ir(acac) structure | US2006835469 |
| | (methyl-quinoline-methylphenyl)₂Ir(acac) structure | US20060202194 |
| | (methyl-quinoline-dimethylphenyl)₂Ir(acac) structure | US20060202194 |
| | (methyl-quinoline-phenyl)₃Ir structure | US20070087321 |

TABLE 1-continued

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| Platinum(II) organometallic complexes | | WO2003040257 |

TABLE 1-continued
| MATERIAL | EXAMPLES OF MATERIAL | PUBLICATIONS |
| --- | --- | --- |
| Osmium(III) complexes | 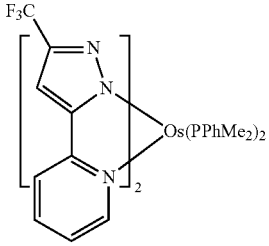 | Chem. Mater. 17, 3532 (2005) |
| Ruthenium(II) complexes | 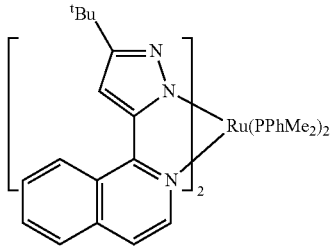 | Adv. Mater. 17, 1059 (2005) |
| Rhenium (I), (II), and (III) complexes | 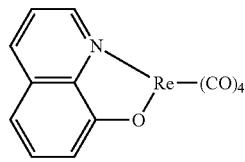 | US20050244673 |
| Green dopants | | |
| Iridium(III) organometallic complexes | 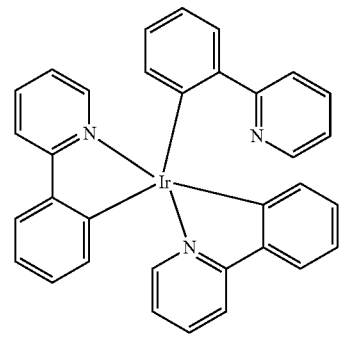<br>and its derivatives | Inorg. Chem. 40, 1704 (2001) |
| | 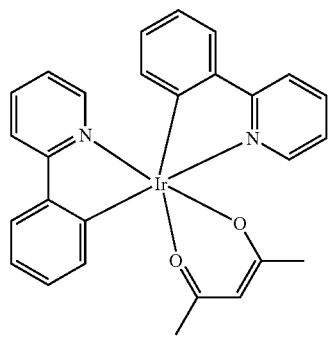 | US20020034656 |

TABLE 1-continued

| MATERIAL | EXAMPLES OF MATERIAL | PUBLICATIONS |
|---|---|---|
| | | US7332232 |
| | | US20090108737 |
| | | US20090039776 |
| | | US6921915 |

TABLE 1-continued

| MATERIAL | EXAMPLES OF MATERIAL | PUBLICATIONS |
|---|---|---|
| | | US6687266 |
| | | Chem. Mater. 16, 2480 (2004) |
| | | US20070190359 |
| | | US 20060008670<br>JP2007123392 |
| | | Adv. Mater. 16, 2003 (2004) |

TABLE 1-continued
| MATERIAL | EXAMPLES OF MATERIAL | PUBLICATIONS |
|---|---|---|
| | 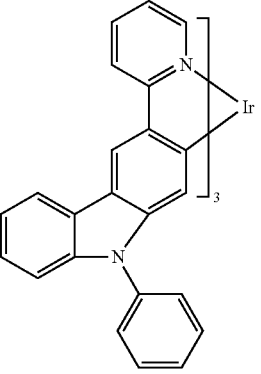 | Angew. Chem. Int. Ed. 2006, 45, 7800 |
| | 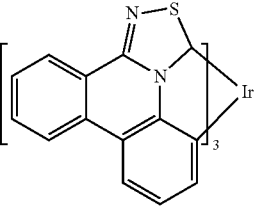 | WO2009050290 |
| | 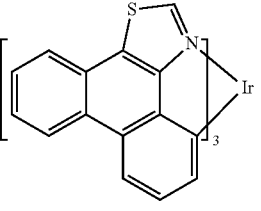 | US20090165846 |
| | 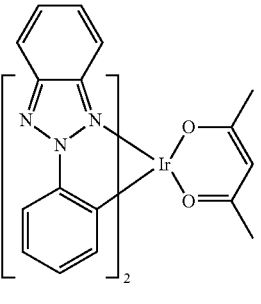 | US20080015355 |
| Monomer for polymeric metal organometallic compounds | 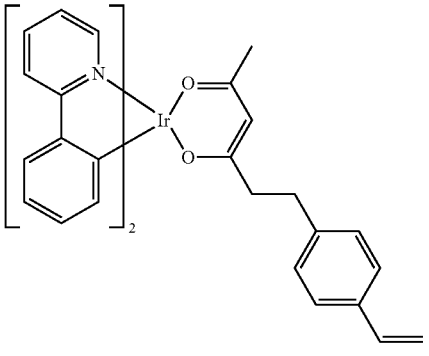 | US7250226, US7396598 |

TABLE 1-continued

| MATERIAL | EXAMPLES OF MATERIAL | PUBLICATIONS |
|---|---|---|
| Pt(II) organometallic complexes, including polydentated ligands | | Appl. Phys. Left. 86, 153505 (2005) |
| | | Appl. Phys. Lett. 86, 153505 (2005) |
| | | Chem. Lett. 34, 592 (2005) |
| | | WO2002015645 |
| | | US20060263635 |

TABLE 1-continued
| MATERIAL | EXAMPLES OF MATERIAL | PUBLICATIONS |
|---|---|---|
| Cu complexes | 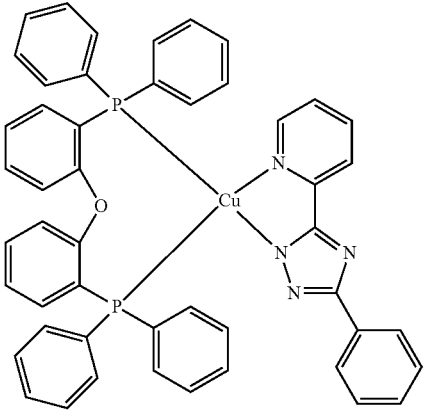 | WO2009000673 |
| Gold complexes | 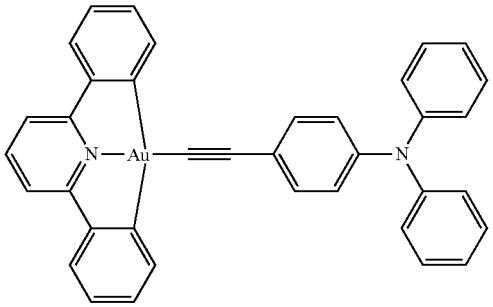 | Chem. Commun. 2906 (2005) |
| Rhenium(III) complexes | 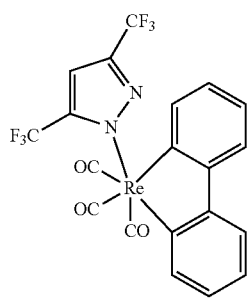 | Inorg. Chem. 42, 1248 (2003) |
| Deuterated organometallic complexes | 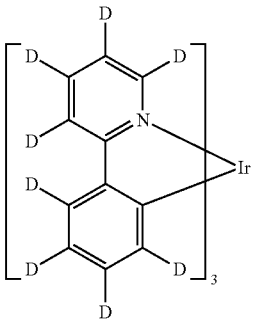 | US20030138657 |

TABLE 1-continued

| MATERIAL | EXAMPLES OF MATERIAL | PUBLICATIONS |
| --- | --- | --- |
| Organometallic complexes with two or more metal centers | | US20030152802 |
| | | US7090928 |
| Blue dopants | | |
| Iridium(III) organometallic complexes | | WO2002002714 |
| | | WO2006009024 |

TABLE 1-continued

| MATERIAL | EXAMPLES OF MATERIAL | PUBLICATIONS |
|---|---|---|
| | | US20060251923 |
| | | US7393599, WO2006056418, US20050260441, WO2005019373 |
| | | US7534505 |
| | | US7445855 |
| | | US20070190359, US20080297033 |
| | | US7338722 |

TABLE 1-continued

| MATERIAL | EXAMPLES OF MATERIAL | PUBLICATIONS |
|---|---|---|
| | | US20020134984 |
| | | Angew. Chem. Int. Ed. 47, 1 (2008) |
| | | Chem. Mater. 18, 5119 (2006) |
| | | Inorg. Chem. 46, 4308 (2007) |
| | | WO2005123873 |
| | | WO2005123873 |

TABLE 1-continued
| MATERIAL | EXAMPLES OF MATERIAL | PUBLICATIONS |
|---|---|---|
| | 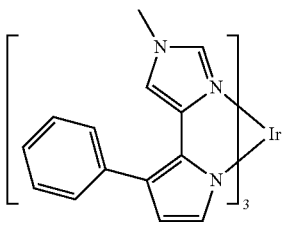 | WO2007004380 |
| | 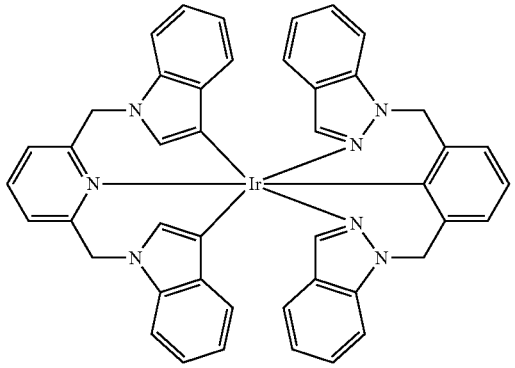 | WO2006082742 |
| Osmium(II) complexes | 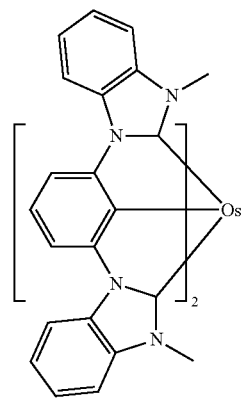 | US7279704 |
| | 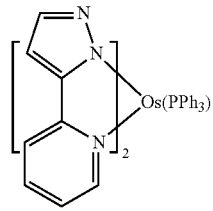 | Organometallics 23, 3745 (2004) |
| Gold complexes | 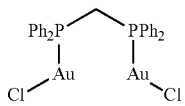 | Appl. Phys. Lett. 74, 1361 (1999) |
| Platinum(II) complexes | 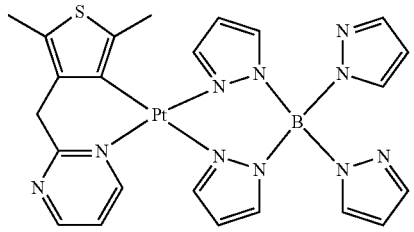 | WO2006098120, WO2006103874 |

TABLE 1-continued
| MATERIAL | EXAMPLES OF MATERIAL | PUBLICATIONS |
|---|---|---|
| Exciton/hole blocking layer materials | | |
| Bathocuprine compounds (e.g., BCP, BPhen) | 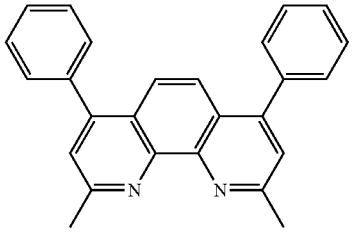 [SMILES: Cc1cc(-c2ccccc2)c2ccc3c(-c4ccccc4)cc(C)nc3c2n1] | Appl. Phys. Lett. 75, 4 (1999) |
| | 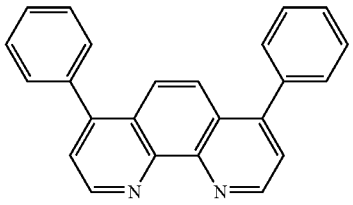 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 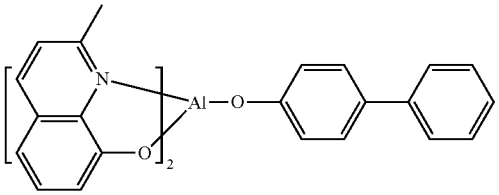 | Appl. Phys. Lett. 81, 162 (2002) |
| 5-member ring electron deficient heterocycles such as triazole, oxadiazole, imidazole, benzoimidazole | 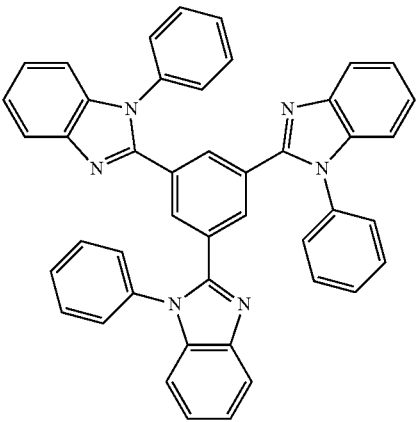 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 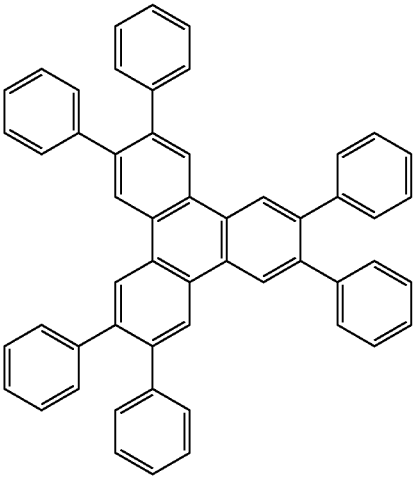 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 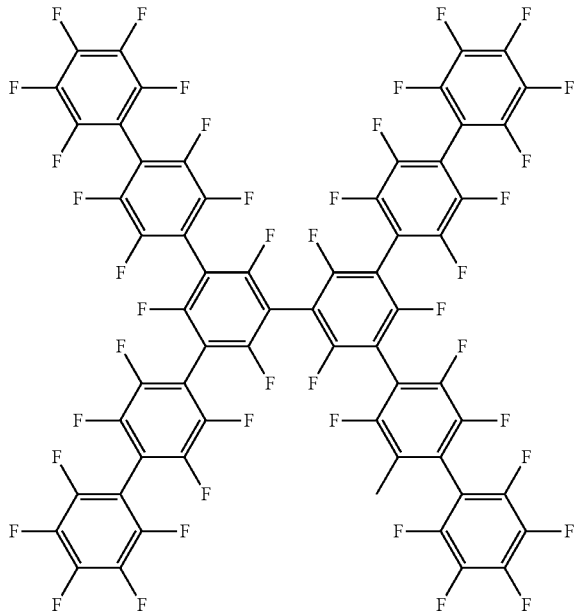 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 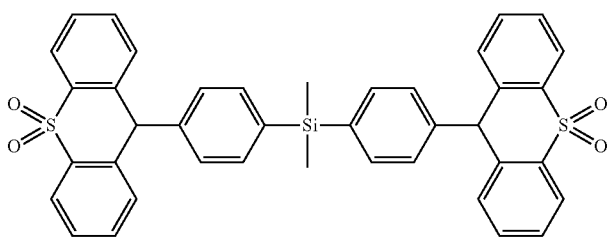 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |

TABLE 1-continued

| MATERIAL | EXAMPLES OF MATERIAL | PUBLICATIONS |
|---|---|---|
| Electron transporting materials | | |
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) US7230107 |

TABLE 1-continued

| MATERIAL | EXAMPLES OF MATERIAL | PUBLICATIONS |
| --- | --- | --- |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 1-continued
| MATERIAL | EXAMPLES OF MATERIAL | PUBLICATIONS |
|---|---|---|
| Silole compounds | 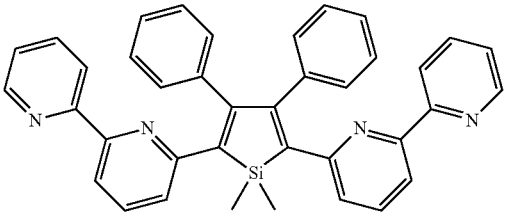 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 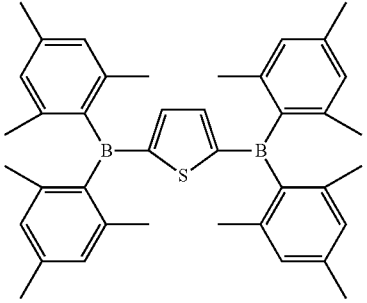 | J. Am. Chem. Soc. 120, 9714 (1998) |
| Fluorinated aromatic compounds | 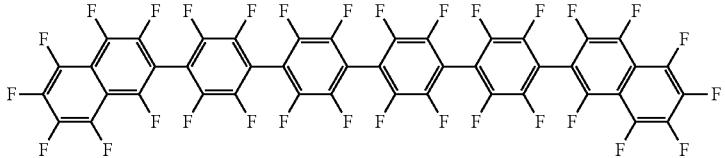 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 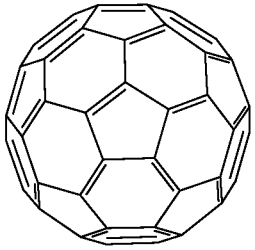 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 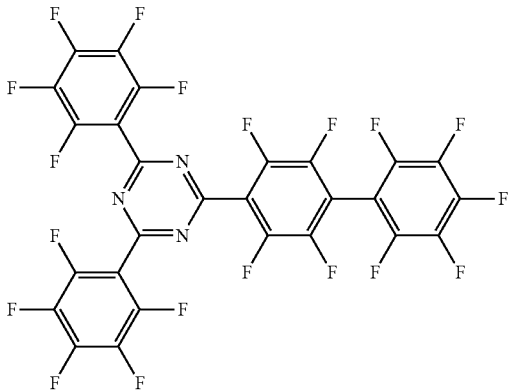 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

| MATERIAL | EXAMPLES OF MATERIAL | PUBLICATIONS |
|---|---|---|
| Zn (N^N) complexes | 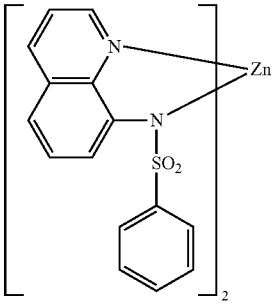 | US6528187 |

EXAMPLES

Example 1

Compound H-1

1. Synthesis of Dibenzoselenophene

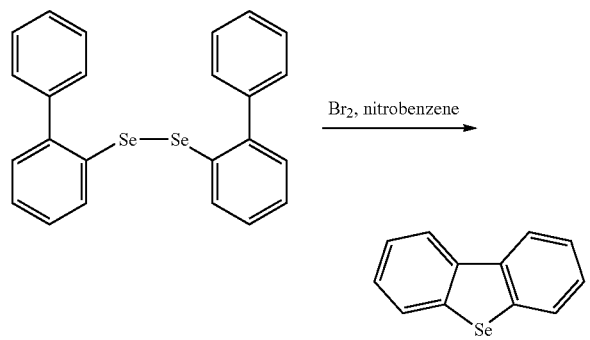

A mixture of 10 g (21.5 mmol) of 1,2-di(biphenyl-2-yl)diselane (synthesized according to J. Am. Chem. Soc. 1950, 72, 5753-5754), 3.45 g (21.5 mmol) of bromine and 30 mL of nitrobenzene was heated at 110° C. for 3.5 hours. Then the reaction mixture was cooled and nitrobenzene was removed by vacuum distillation. The residue was purified by silica gel column chromatography using 10% methylene chloride in hexane as the elutent. 9.8 g of white solids were obtained as the product which was confirmed by MS.

2. dibenzoselenophen-4-ylboronic acid

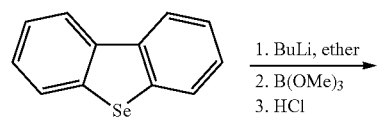 1. BuLi, ether
2. B(OMe)$_3$
3. HCl

-continued

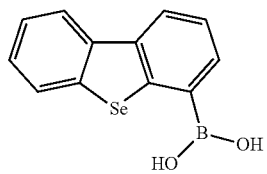

4.0 g (17.3 mmol) of dibenzoselenophene and 150 mL of dry ether were added in a 250 mL three necked flask under nitrogen. To the mixture, 11.5 mL of BuLi (1.6 M in hexane) was added slowly at room temperature. The reaction mixture was then heated to reflux for 5 hours. The reaction mixture was cooled to −78° C. and 5 mL of trimethyl borate was added. It was then left to stir at room temperature for overnight. About 50 mL of 1 M HCl was added to the reaction mixture. The organic phase was extracted with ethyl acetate and dried with sodium sulfate. The combined organic phase was evaporated to dryness and 100 mL of 30% ethyl acetate in hexane was added to the solid with stirring at room temperature for 8 hours. The suspension was filtered, the solids were washed with hexane and dried, yielding 2 of white solids as the product which was confirmed by NMR 3. Synthesis of Compound H-1

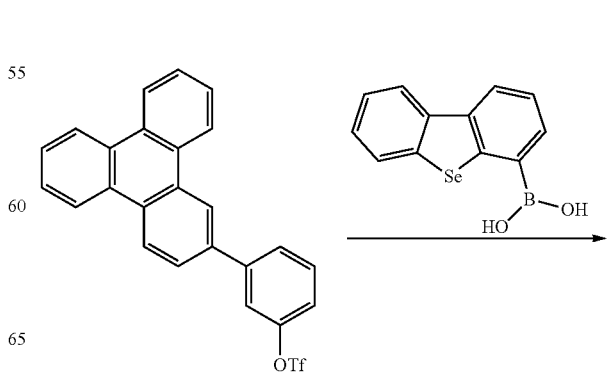

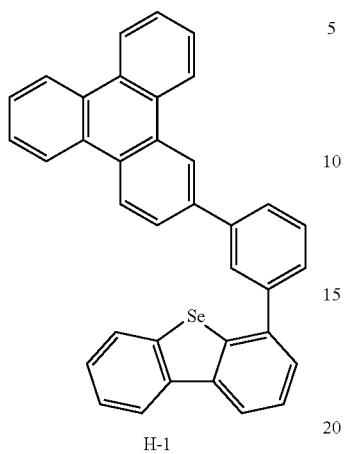

H-1

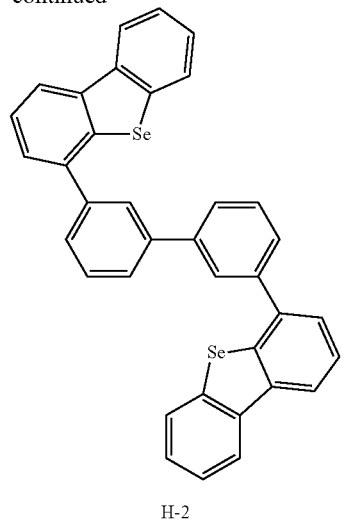

H-2

1.0 g (3.6 mmol) of dibenzoselenophen-4-ylboronic acid, 1.51 g (3.3 mmol) of triphenylenephenyl triflate (synthesized according to the method disclosed in Example 3 below), 0.15 g (0.16 mmol) of Pd$_2$(dba)$_3$, 0.27 g (0.66 mmol) of dicyclohexylphosphino-2',6'-dimethoxybiphenyl, 4.2 g of K$_3$PO$_4$, 90 mL of toluene and 10 mL of water were added in a 250 mL three necked flask. The reaction mixture was bubbled with nitrogen for 20 mins and heated to reflux for overnight under nitrogen. The reaction mixture was dried and purified by silica gel column chromatography with 15% methylene chloride in hexane as elutent. ~1.35 g of white solids were obtained as the product which was confirmed by NMR.

1.67 g (6.0 mmol) of dibenzoselenophen-4-ylboronic acid, 1.20 g (2.6 mmol) of biphenyl-4,4'-diylbis(trifluoromethanesulfonate), 0.025 g (0.027 mmol) of Pd$_2$(dba)$_3$, 0.045 mg (0.11 mmol) of dicyclohexylphosphino-2',6'-dimethoxybiphenyl, 1.7 g of K$_3$PO$_4$, 90 mL of toluene and 10 mL of water were added in a 250 mL three necked flask. The reaction mixture was bubbled nitrogen for 20 mins and then heated to reflux for overnight under nitrogen. The reaction mixture was dried and the residue was purified by silica gel column chromatography with 10% methylene chloride in hexane as elutent. ~1.31 g of white solids was obtained as the product which was confirmed by NMR.

Example 3 method of preparing 3-(triphenylen-2-yl)phenyl trifluoromethanesulfonate (triphenylenephenyl triflate)

Example 2

Compound H-2

1. Synthesis of Compound H-2

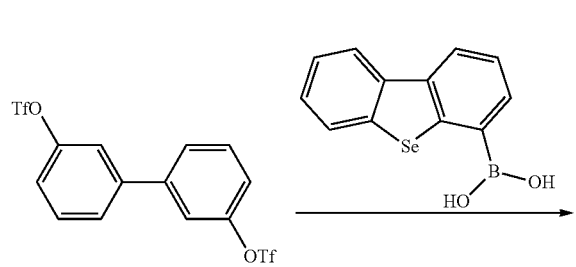

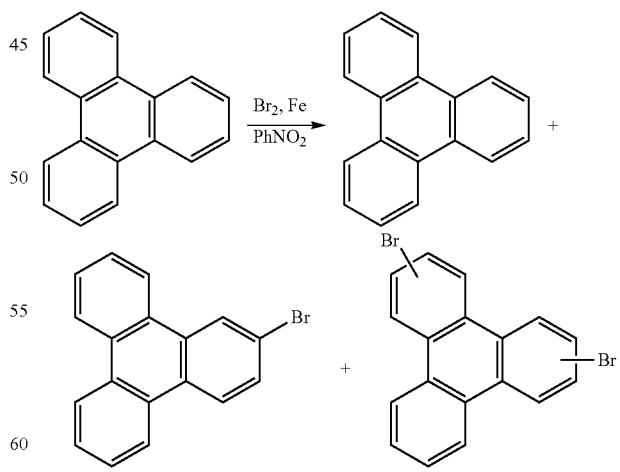

Triphenylene (19.0 g, 83 mmol) was added to and 600 mL of nitrobenzene. After all the triphenylene had dissolved, iron powder (0.07 g, 125 mmol) was added. The reaction flask was put in an ice bath. Bromine (20.0 g 125 mmol) in 50 mL of nitrobenzene was slowly added via addition funnel. After that, the reaction was stirred in an ice bath for 5 hours. HPLC was performed to monitor the reaction (TLC did not show separation of triphenylene and bromotriphenylenes). When the ratio of triphenylene:2-bromotriphenylene:dibromotriphenylenes reached approximately 2:7:1 (at 254 nm), the reaction was quenched by adding a Na$_2$SO$_3$ solution. The mixture was then extracted with CH$_2$Cl$_2$. The combined organic extract was dried over MgSO$_4$ and the CH$_2$Cl$_2$ was removed by rotovap. The remaining nitrobenzene was removed by vacuum distillation to yield the crude bromotriphenylene product which was used without further purification.

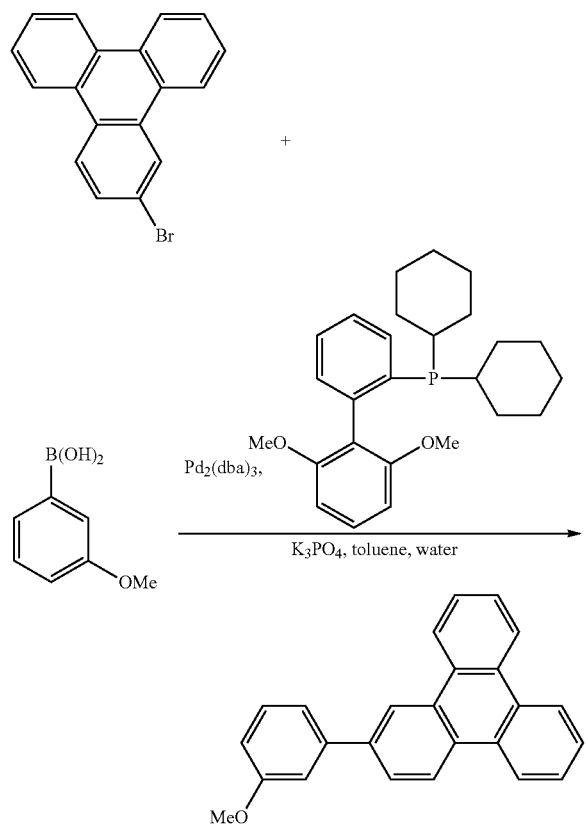

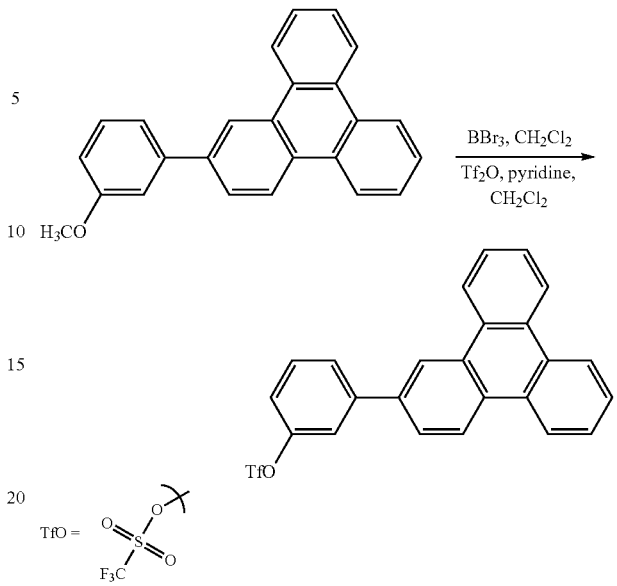

12 g (39 mmol) bromotriphenylene mixture containing a 2:7:1 mixture of unreacted triphenylene, monobromo and dibromo triphenylene, 13 g (86 mmol) 3-phenylboronic acid, 0.6 g (1.56 mmol) 2-dicyclohexylphosphino-2',6'-dimethoxybiphenyl and 25 g (117 mmol) potassium phosphate tribasic (K$_3$PO$_4$) are weighed in a round bottom flask. 150 mL toluene and 80 mL water were added to the flask as solvent. The solution was purged with nitrogen and 0.4 g (0.39 mmol) of tris(dibenzylideneacetone)dipalladium (0) [Pd$_2$(dba)$_3$] was added. The solution was heated to reflux for twelve hours. Upon cooling, the organic layer was separated, and dried with MgSO$_4$. The product was readily separated by column chromatography from triphenylene and di-(3-methoxyphenyl) substituted triphenylene using Hexane/dichloromethane as eluent (1/0 gradient to 3/2). The solvent was removed by rotary evaporation, and the product, 2-(3-methoxyphenyl)triphenylene, was dried overnight under vacuum.

In a round bottom flask under nitrogen, 1.8 g (5.4 mmol) 2-(3-methoxyphenyl)triphenylene was dissolved in 25 mL anhydrous dichloromethane. The solution was cooled to −78° C. and 4 g (1.5 mL, 16 mmol) boron tribromide was added slowly via syringe. The solution was warmed to room temperature and stirred overnight. Ice was carefully added to quench unreacted BBr$_3$. The 3-(triphenylen-2-yl)phenol intermediate precipitated upon addition of ice, and dichloromethane was added to dissolve. The organic layer was separated and dried with MgSO$_4$, the dichloromethane was removed by rotary evaporation and the product was dried under vacuum.

1.7 g (5.3 mmol) of 3-(triphenylen-2-yl)phenol was added to a flask under nitrogen with 0.84 g (10.5 mmol) anhydrous pyridine and 100 mL anhydrous dichloromethane. The solution was cooled in an ice bath and 2.97 g (10.5 mmol) trifluoromethanesulfonic anhydride (Tf$_2$O) was added slowly via syringe. The solution was warmed to room temperature and stirred overnight. The solution was washed with water, dried with MgSO$_4$ and the solvent was removed by rotary evaporation. The product, 3-(triphenylen-2-yl)phenyl trifluoromethanesulfonate, was purified by column chromatography using hexane/dichloromethane as eluent (1/0 to 1/1 gradient).

Description of the method of synthesis can also be found in U.S. provisional application No. 60/963,944, corresponding to International Application No: PCT/US08/72452, filed Aug. 7, 2008, which is incorporated herein by reference in its entirety.

Example 4

Device Examples

All example devices were fabricated by high vacuum (<10$^{-7}$ Torr) thermal evaporation. The anode electrode is 1200 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of H$_2$O and O$_2$) immediately after fabrication, and a moisture getter was incorporated inside the package.

The organic stack of the device examples consisted of sequentially, from the ITO surface, 100 Å of Compound A as the hole injection layer (HIL), 300 Å of 4,4'-bis[N-(1-naphthyl)-N-phenylamino]biphenyl (α-NPD) as the hole transporting layer (HTL), 300 Å of the invention compound doped with 10 or 15 wt % of an Ir phosphorescent compound as the emissive layer (EML), 50 Å of HPT or 100 Å of the invention compound as the ETL2 and 450 or 400 Å of Alq$_3$ (tris-8-hydroxyquinoline aluminum) as the ETL1.

Comparative Examples 1 and 2 were fabricated similarly to the Device Examples except that the CBP is used as the host.

The device structures and data are summarized in Tables 2 and 3, where Table 2 shows device structure and Table 3 shows corresponding measured results for those devices. As used herein, Compounds A and B, and HPT, have the following structures:

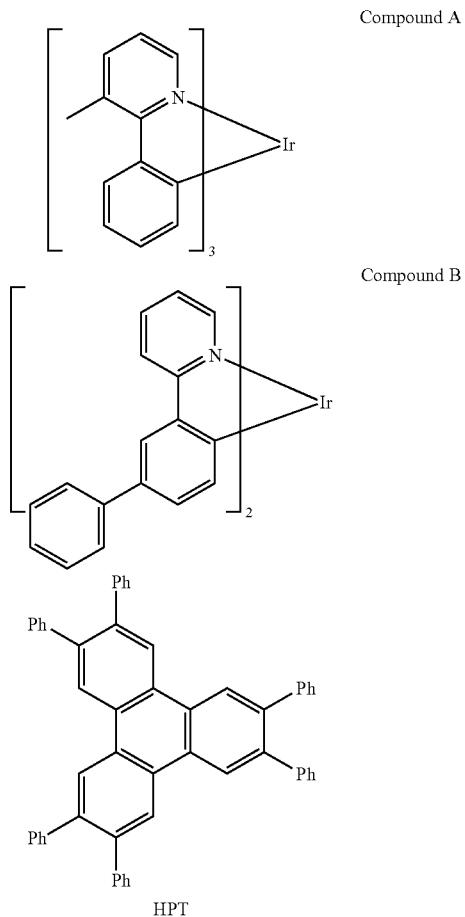

Compound A

Compound B

HPT

TABLE 2

| Device Example | Host | Dopant % | ETL2 (Å) | ERA (Å) |
|---|---|---|---|---|
| Comparative 1 | CBP | B 10% | HPT (50) | Alq$_3$ (450) |
| Comparative 2 | CBP | A 10% | HPT (50) | Alq$_3$ (450) |
| 1 | H-1 | A 10% | HPT (50) | Alq$_3$ (450) |
| 2 | H-1 | A 10% | H-1 (100) | Alq$_3$ (400) |
| 3 | H-1 | A 15% | HPT (50) | Alq$_3$ (450) |
| 4 | H-1 | A 15% | H-1 (100) | Alq$_3$ (400) |
| 5 | H-2 | A 10% | HPT (50) | Alq$_3$ (450) |
| 6 | H-2 | A 10% | H-2 (100) | Alq$_3$ (400) |

TABLE 2-continued

| Device Example | Host | Dopant % | ETL2 (Å) | ERA (Å) |
|---|---|---|---|---|
| 7 | H-2 | A 15% | HPT (50) | Alq$_3$ (450) |
| 8 | H-2 | A 15% | H-2 (100) | Alq$_3$ (400) |

TABLE 3

| | At L = 1000 cd/m$^2$ | | | | | At J = 40 mA/cm$^2$ | |
|---|---|---|---|---|---|---|---|
| Device Example | CIE X | CIE Y | V (V) | LE (cd/A) | EQE (%) | PE (lm/W) | $L_0$ (cd/m$^2$) | $LT_{80\%}$ (hr) |
| Comparative 1 | 0.331 | 0.627 | 6.1 | 61.0 | 17 | 31.4 | 16,935 | 87 |
| Comparative 2 | 0.346 | 0.613 | 6.2 | 57.0 | 16 | 28.9 | 13,304 | 105 |
| 1 | 0.357 | 0.605 | 6.1 | 62.6 | 17.3 | 32.2 | 15,561 | 140 |
| 2 | 0.358 | 0.605 | 6.7 | 56.9 | 15.7 | 26.7 | 15,421 | 150 |
| 3 | 0.362 | 0.604 | 5.8 | 63.3 | 17.4 | 34.3 | 17,977 | 130 |
| 4 | 0.363 | 0.603 | 6.3 | 55.8 | 15.4 | 27.8 | 16,436 | 175 |
| 5 | 0.352 | 0.611 | 6.2 | 61.1 | 16.8 | 30.9 | 16,102 | 126 |
| 6 | 0.351 | 0.610 | 7.3 | 45.6 | 12.6 | 19.6 | 14,384 | 148 |
| 7 | 0.354 | 0.610 | 6.3 | 59.2 | 16.3 | 29.5 | 16,255 | 73 |
| 8 | 0.354 | 0.610 | 7.5 | 36.5 | 10 | 15.3 | 11,882 | 185 |

From Device Examples 1-8, it can be seen that Compounds H-1 and H-2 as hosts in green phosphorescent OLEDs give high device efficiency (LE>40 cd/A at 1000 cd/m$^2$), indicating the dienzoselenophene linked with aryl building blocks such as biphenyls or triphenylenes, have triplet energy high enough for efficient green electrophosphorescence. The high stability of devices incorporating Compounds H-1 and H-2 as the host is notable. Device Example 1 and Comparative Example 2 are only different in the host. Device Example 1 uses Compound H-1 as the host whereas Comparative Example 2 uses the commonly used host CBP. The lifetime, $T_{80\%}$ (defined as the time required for the initial luminance, $L_0$, to decay to 80% of its value, at a constant current density of 40 mA/cm$^2$ at room temperature) are 140 hours and 105 hours respectively, with Device Example 1 having a slightly higher $L_0$. Similarly, Device Example 5 using Compound H-2 as the host, is more stable than Comparative Example 2. It is also notable that the compounds may function well as an enhancement layer material (ETL2). For example, Device Example 8 and Device Example 4 both have Compound H-1 and H-2 as the host and ETL2 layer, respectively. They have $T_{0.8}$ of 185 and 175 hours respectively, indicating the good performance of Compounds H-1 and H-2 as the enhancement layer material.

The data suggest that hosts containing dibenzoselenophenes are excellent host and enhancement layer materials for phosphorescent OLEDs, providing as least the same efficiency and improvement in stability compared to the commonly used CBP as the host. More conjugated versions of triphenylene containing benzoselenophenes, for example triphenylene and dibenzoselenophene units linked via p-phenylene (such as 4,4'-biphenyl) may be very suitable for lower energy (yellow to red) phosphorescent OLEDs. The triphenylene containing group may be attached to any position of benzoselenophenes.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

What is claimed is:

1. An organoselenium compound selected from the group consisting of

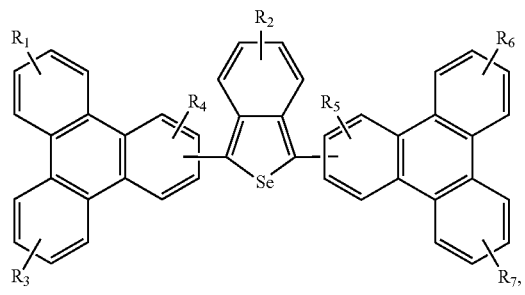

and

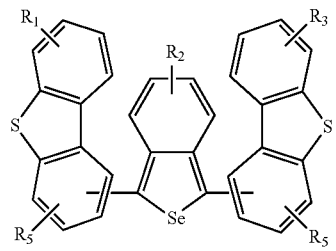

wherein each of $R_1$, $R_2$, $R_3$, $R_4$, $R_5$, $R_6$ and $R_7$ indicates an optional substituent to any possible position in the relevant moiety and each line linking two molecular moieties indicates attachment between the two moieties at any possible positions on the respective moieties.

2. An organic light emitting device, comprising an organic layer positioned between an anode layer and a cathode layer, said organic layer comprising an organoselenium material, wherein said organoselenium material is a compound comprising a benzo[c]selenophene selected from the group consisting of

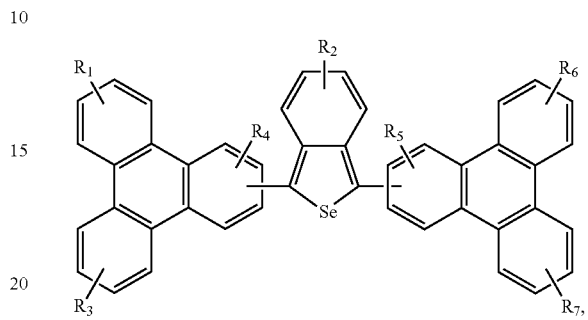

and

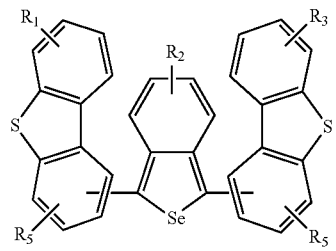

wherein each of $R_1$, $R_2$, $R_3$, $R_4$, $R_5$, $R_6$, and $R_7$ is an optional substituent to any possible position in the relevant moiety, and each line linking two moieties indicates attachment between the two moieties at any possible positions on the respective moieties.

* * * * *